United States Patent

Singh et al.

Patent Number: 5,994,342
Date of Patent: Nov. 30, 1999

[54] 3-(SUBSTITUTED METHYL)-4-OXA-1-AZABICYCLO[3.2.0]HEPTAN-7-ONE DERIVATIVES USEFUL AS ANTITUMOR AGENTS

[75] Inventors: Rajeshwar Singh, Edmonton, Canada; Tomohiro Yamashita, Hidaka, Japan; Charles Fiakpui, Edmonton, Canada; George Thomas, Edmonton, Canada; Chan Ha, Edmonton, Canada; Hiroshi Matsumoto; Toshio Otani, both of Tokushima, Japan; Shinji Oie, Tokyo, Japan; Ronald Micetich, Sherwood Park, Canada

[73] Assignees: Taiho Pharmaceutical Co., Ltd., Tokyo, Japan; Synphar Laboratories Inc., Alberta, Canada

[21] Appl. No.: 08/513,802
[22] PCT Filed: Jan. 6, 1995
[86] PCT No.: PCT/GB95/00024
  § 371 Date: Aug. 5, 1998
  § 102(e) Date: Aug. 5, 1998
[87] PCT Pub. No.: WO95/18807
  PCT Pub. Date: Jul. 13, 1995

[30] Foreign Application Priority Data

Jan. 7, 1994 [GB] United Kingdom .................. 9400220

[51] Int. Cl.⁶ ......................... C07D 503/00; A61K 31/42
[52] U.S. Cl. ............................ 514/210; 540/347
[58] Field of Search .............................. 540/347; 514/210

[56] References Cited

U.S. PATENT DOCUMENTS 4,202,819  5/1980  Kellett et al. ........................ 260/245.3

FOREIGN PATENT DOCUMENTS

| 34 27 651A1 | 6/1985 | Germany . |
| 2702091 | 7/1997 | Germany . |
| 1515241 | 6/1978 | United Kingdom . |
| 1585661 | 3/1981 | United Kingdom . |

OTHER PUBLICATIONS

International Publication No. WO 94/01109 published Jan. 20, 1994.

*Primary Examiner*—Mukund J. Shah
*Assistant Examiner*—Bruck Kifle
*Attorney, Agent, or Firm*—Nikaido Marmelstein Murray & Oram, LLP.

[57] ABSTRACT

The present invention is based on the discovery that certain 3-(substituted methyl)-4-oxa-1-azabicyclo[3.2.0]heptan-7-one derivatives of formula I or a pharmaceutically acceptable salt thereof are useful as antitumor agents against sensitive and resistant tumor cells.

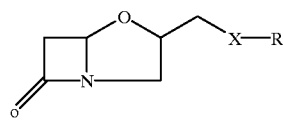

(I)

Wherein X is NH or O, and R is defined in the specification.

9 Claims, No Drawings

3-(SUBSTITUTED METHYL)-4-OXA-1-AZABICYCLO[3.2.0]HEPTAN-7-ONE DERIVATIVES USEFUL AS ANTITUMOR AGENTS

The present invention relates to novel 3-(substituted methyl)-4-oxa-1-azabicyclo[3.2.0]heptan-7-one derivatives, and to the preparation of such compounds, and to their incorporation in pharmaceutical compositions, and to their use as pharmacological agents, in particular for use in anti-cancer treatment.

BACKGROUND OF THE INVENTION

Since the invention of G0069A (JP 61-212587) and Tü 1718 (DE 3727651), we paid attention to develop β-lactam class of compounds as antitumor agents. However, there were a lot of difficulties to obtain these compounds in large scales. For example, only 20 mg of G0069A was isolated from 10 L fermentation broth even after under well controlled fermentation techniques and suitable experimental conditions. On the other hand, another β-lactam compound having the same stereochemistry at $C_5$, (3R,5S)-3-hydroxymethyl-4-oxa-1-azabicyclo[3.2.0]heptan-7-one (clavam 1, G0069B) was isolated by Brown and Evans (J. Chem. Soc. Chem. Comm. 1979, 282) from the culture of *Streptomyces clavuligerus*, which is reported to exhibit antifungal activity. We have synthesized clavam 1 and have done extensive biological evaluation. We found that clavam 1 exhibit excellent antitumor activity both in vitro and in vivo but is chemically unstable.

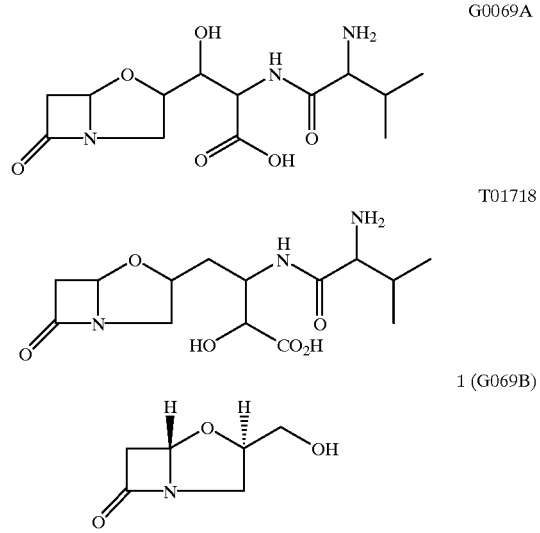

The chemical unstability may be due to the intermolecular interaction of —OH to the β-lactam ring which results in the decomposition of product.

As a part of the program directed toward the development of β-lactam class of compounds as novel antitumor agents, it is necessary to get compounds which are relatively easy to synthesize, chemically stable and have strong antitumor activity.

SUMMARY OF THE INVENTION

The present invention is based on the discovery that certain 3-(substituted methyl)-4-oxa-1-azabicyclo[3.2.0] heptan-7-one derivatives exhibit excellent activity against sensitive and resistant tumor cells.

In accordance with the present invention, there is provided a 3-(substituted methyl)-4-oxa-1-azabicyclo[3.2.0]heptan-7-one derivative of general formula I or pharmaceutically acceptable salt thereof,

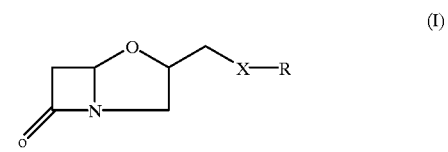

wherein X is NH or O,
when X is NH,
  R is hydrogen, —$COR_1$, wherein $R_1$ is (i) a $C_1$–$C_6$ alkyl group which may be substituted by 1–3 substituents selected from halogen, hydroxy, formyloxy, azido, carboxyl, heteroaryl or acetamide, (ii) a $C_2$–$C_4$ alkenyl group, (iii) a $C_2$–$C_4$ alkynyl group, (iv) a $C_3$–$C_6$ cycloalkyl group, (v) a phenyl group which may be substituted by 1–3 substituents selected from hydroxy, halogen, $C_1$–$C_6$ alkoxy group or cyano, (vi) a $C_5$–$C_6$ heteroaryl group, (vii) a $NR_2R_3$ wherein $R_2$ and $R_3$ are the same or different and each is a hydrogen, $C_1$–$C_6$ alkyl group or (7-oxo-1-aza-4-oxabicyclo[3.2.0]hept-3-yl)methyl group or (viii) benzyloxy group;
  —$SO_2R_4$ wherein $R_4$ is a $C_1$–$C_6$ alkyl group or a phenyl group which may be substituted by 1–3 substituents selected from $C_1$–$C_6$ alkyl group, halogen or $C_1$–$C_6$ alkoxy group;
  1-2 amino acid residue which may be substituted with protective group,
when X is O,
  R is 1-2 amino acid residue which may be substituted with protective group.
  The pharmaceutically acceptable salts of formula I are selected from sodium, potassium, magnesium, calcium, hydrogen chloride, tartaric acid, succinic acid, fumaric acid or p-toluenesulfonic acid.
  Examples of $C_1$–$C_6$ alkyl group as substitutents in $R_1$, $R_2$, $R_3$ or $R_4$ are straight or branched chain alkyl group having 1–6 carbon atoms such as methyl, ethyl, propyl, isopropyl, butyl, isobutyl, sec-butyl, tert-butyl, pentyl, 3-methylbutyl, hexyl and the like.
  Examples of halogen atoms as substituents in $R_1$ or $R_4$ are fluorine, chlorine, bromine or iodine.
  Examples of heteroaryl group in $R_1$ are 1,2,3-triazole, 1,2,4-triazole, thiophene, pyridine and the like.
  Examples of $C_2$–$C_4$ alkenyl group as defined in $R_1$ are alkenyl groups having 2–4 carbon atoms such as ethenyl, 1-propenyl, 2-propenyl, 1-butenyl, 3-butenyl and the like.
  Examples of $C_2$–$C_4$ alkynyl group as defined in $R_1$ are ethynyl, 1-propynyl, 2-propynyl, 1-butynyl, 3-butynyl and the like.
  Examples of $C_3$–$C_6$ cycloalkyl group as defined in $R_1$ are cyclopropyl, cyclobutyl, cyclopentyl, cyclohexyl and the like.
  Examples of heteroaryl group or heteroaryl substituent in $R_1$ are $C_5$–$C_6$ heteroaryl group which may have 1–3 heteroatoms selected from nitrogen and sulfur such as 1,2,3-triazole, 1,2,4 triazole, thiophene, pyridine and the like.
  Example of $C_1$–$C_6$ alkoxy group as substituents in $R_1$ or $R_4$ are methoxy, ethoxy, propyloxy, butyloxy, pentyloxy, hexyloxy and the like.
  The term "amino acid residue" used herein refers to the remaining group after the removal of the hydroxy group from a carboxy group of an amino acid. The term "1-2 amino acid" used herein is one amino acid or one dipeptide constituted of two amino acids which are bonded each other through a peptide bond.

Example of amino acid are α-amino acids which compose organisms protein or their optical isomers such as glycine, D- or L-alanine, D- or L-valine, D- or L-leucine, D- or L-isoleucine, D- or L-serine, D- or L-threonine, D- or L-aspartic acid, D- or L-glutamic acid, D- or L-asparagine, D- or L-glutamine, D- or L-lysine, D- or L-arginine, D- or L-cysteine, D- or L-cystine, D- or L-methionine, D- or L-phenylalanine, D- or L-tyrosine, D- or L-tryptophane, D- or L-histidine, D- or L-proline and the like.

Examples of protective group in amino acid residue are benzyl and/or acyl group such as acetyl, 2-thienylacetyl, benzyloxycarbonyl, tert-butoxycarbonyl and the like.

Preferably, the derivatives of formula I wherein X is NH and R is —COR$_1$ wherein R$_1$ is C$_1$–C$_6$ alkyl group which may be substituted by 1–3 substituents selected from halogen, hydroxy, formyloxy, azido, carboxy, heteroaryl or acetamido.

Preferably, the derivatives of formula I wherein X is NH and R is —COR$_1$ wherein R$_1$ is a NR$_2$R$_3$ wherein R$_2$ and R$_3$ are the same or different and each is a hydrogen, C$_1$–C$_6$ alkyl group or (7-oxo-1-aza-4-oxabicyclo[3.2.0]hept-3-yl)methyl group.

Preferably, the derivatives of formula I wherein X is NH or O and R is 1-2 amino acid residue which may be substituted with protective group.

Preferably, the derivative of formula I wherein X is NH, having (3R,5R) or (3S,5S) configuration at two asymmetric carbons on 4-oxa-1-azabicyclo[3.2.0]heptan-7-one ring system or the mixture of them.

Preferably, the derivative of formula I wherein X is O, having (3R,5S) or (3S,5R) configuration at two asymmetric carbons on 4-oxa-1-azabicyclo[3.2.0]heptan-7-one ring system or the mixture of them.

More specifically, when X is NH in general formula I, R is:

hydrogen

COR$_1$ wherein R$_1$ is selected from methyl, propyl, 1-methylethyl, chloromethyl, azidomethyl, (1,2,3-triazol-1-yl)methyl, formyloxymethyl, hydroxymethyl, trifluoromethyl, pentyl, 5-bromopentyl, 5-formyloxypentyl, 5-azidopentyl, 5-(1,2,3-triazol-1-yl)pentyl, 5-(acetamido)pentyl, cyclohexyl, 2-carboxyethyl, benzyloxy, phenyl, 4-hydroxyphenyl, 4-methoxyphenyl, 3,4-dimethyoxyphenyl, 4-fluorophenyl, 2,5-difluorophenyl, 2,4,5-trifluorophenyl, 4-cyanophenyl, thiophen-2-yl-methyl, pyridin-3-yl, diethylamino, (7-oxo-1-aza-4-oxabicyclo[3.2.0]hept-3-yl)methylamino, 3-butenyl, ethynyl, aminomethyl, N-acetylaminomethyl, N-(L-2-N-benzyloxycarbonylamino-3-methylbutyryl)aminomethyl, N-(L-2-amino-3-methylbutyryl)aminomethyl, N-(L-2-N-benzyloxycarbonylamino-3-benzyloxycarbonylpropanoyl)aminomethyl, N-(L-2-amino-3-carboxypropanoyl)aminomethyl, N-(D-4-N-benzyloxycarbonylamino-4-benzyloxycarbonylbutyryl)aminomethyl, N-(D-4-amino-4-carboxybutyryl)aminomethyl, L-1-N-benzyloxycarbonylaminoethyl, L-1-aminoethyl, D-1-N-benzyloxycarbonylaminoethyl, D-1-aminoethyl, L-1-N-benzyloxycarbonylamino-2-methylpropyl, L-1-amino-2-methylpropyl, D-1-N-benzyloxycarbonylamino-2-methylpropyl, D-1-amino-2-methylpropyl), L-1-N-benzyloxycarbonylamino-2-phnylethyl, L-1-amino-2-phenylethyl, L-1-N-benzyloxycarbonylamino- 2-phenylethyl, L-1-N-(L-2-N-benzyloxycarbonylamino-3-benzyloxycarbonylpropanoyl)amino-2-phenylethyl, L-1-N-(L-2-amino-3-carboxypropanoyl)amino-2-phenylethyl, L-1-N-benzyloxycarbonylamino-2-benzyloxycarbonylethyl, L-1-amino-2-carboxyethyl, D-3-N-benzyloxycarbonylamino-3-benzyloxycarbonylpropyl, D-1-amino-3-carboxypropyl, L-3-N-benzyloxycarbonylamino-2-hydroxyethyl or L-1-amino-2-hydroxyethyl.

SO$_2$R$_4$ wherein R$_4$ is selected from methyl, 4-methylphenyl, 4-chlorophenyl or 4-methoxyphenyl group.

When X is O in general formula I, R is;

COR$_1$ wherein R$_1$ is selected from aminomethyl, N-(N-benzyloxycarbonylaminoacetyl)aminomethyl, N-(aminoacetyl)aminomethyl, N-(L-2-N-benzyloxycarbonylaminopropanoyl)aminomethyl, N-(L-2-aminopropanoyl)aminomethyl, N-(L-2-N-benzyloxycarbonylamino-3-methylbutyryl)aminomethyl, N-(L-2-N-benzyloxycarbonylamino-3-methylbutyryl)aminomethyl, N-(L-2-amino-3-methylbutyryl)aminomethyl, L-1-N-(benzyloxycarbonyl)aminoethyl, L-1-aminoethyl, L-1-N-(L-2-N-benzyloxycarbonylamino-3-methylbutyryl)aminoethyl, L-1-N-(L-2-N-amino-3-methylbutyryl)aminoethyl, D-1-N-(benzyloxycarbonyl)aminoethyl, D-1-aminoethyl, D-1-N-[D-2-N-(thiophen-2-yl)acetamidopropanoyl]aminoethyl, L-1-N-(benzyloxycarbonylamino-2-methyl)propyl, L-1-amino-2-methylpropyl, L-1-N-(2-N-benzyloxycarbonylaminoacetyl)amino-2-methylpropyl, L-1-N-(2-aminoacetyl)amino-2-methylpropyl, L-1-N-(L-2-N-benzyloxycarbonylamino-3-methylbutyryl)amino-2-methylpropyl, L-1-N-(L-2-amino-3-methylbutyryl)amino-2-methylpropyl, L-1-N-(L-2-amino-3-carboxypropanoyl)amino-2-methylpropyl, L-1-N-(L-2-N-benzyloxycarbonylamino-3-benzyloxycarbonylpropanoyl)amino-2-methylpropyl, D-1-N-benzyloxycarbonylamino-2-methylpropyl, D-1-amino-2-methylpropyl, D-1-acetamido-2-methylpropyl, D-1-N-(D-2-N-benzyloxycarbonylamino-3-methylbutyryl)amino-2-methylpropyl, D-1-N-(D-2-amino-3-methylbutyryl)amino-2-methylpropyl, L-1-N-(benzyloxycarbonyl)amino-2-phenylethyl, L-1-amino-2-phenylethyl, L-2-N-benzyloxycarbonylamino-2-benzyloxycarbonylethyl, L-2-amino-2-carboxyethyl, L-1-benzyloxycarbonylamino-2-benzyloxycarbonylethyl, L-1-amino-2-carboxyethyl, D-1-benzyloxycarbonylamino-3-benzyloxycarbonylpropyl, D-1-amino-3-carboxypropyl, L-1-benzyloxycarbonylamino-2-benzyloxyethyl, L-1-N-(D-2-N-benzyloxycarbonylaminopropanoyl)amino-2-hydroxyethyl, L-1-N-benzyloxycarbonylamino-2-hydroxyethyl, L-1-N-(D-2-N-benzyloxycarbonylaminopropanoyl)amino-2-benzyloxyethyl, L-1-N-(L-2-N-benzyloxycarbonylamino-3-methylbutyryl)amino-2-benzyloxyethyl, L-1-N-(L-2-amino-3-methylbutyroyl)amino-2-benzyloxyethyl, L-1-acetamido-2-acetyloxyethyl, L-1-acetamido-2-hydroxyethyl, L-[1,5-di-(benzyloxy-carbonylamino)pentyl], L-[1,5-di-(acetamido)pentyl] or L-5-acetamido-1-N-benzyloxycarbonylaminopentyl.

Examples of pharmaceutically acceptable salts are sodium, potassium, calcium, magnesium or hydrogen chloride, tartaric acid, succinic acid, fumaric acid or p-toluenesulfonic acid.

Compounds of formula I may be utilized as antitumor active compounds in medicaments, being formulated with a pharmaceutically acceptable carrier.

The bicyclic nucleus carries two asymmetric carbon atoms at position 3 and 5 and can exist as 4-diastereoisomers. In general, the preferred isomer is that in which the hydrogen atoms at $C_3$ and $C_5$ are trans to each other for superior toxicity against different malignant cells such as P388, KB, NUGC4, WI38, L-1210, sarcoma 180 and colon 26. Such diasterioisomers and their racemic mixtures are also included within the use of the oxapenam derivatives as antitumor agents.

Antitumor activity of compounds described above is expected against some solid cancers such as stomach, lung, breast, liver, uterus and leukemia and so on.

DESCRIPTION OF PREFERRED EMBODIMENT

The present invention relates to the certain 3-(substituted methyl)-4-oxa-1-azabicyclo[3.2.0]heptan-7-one derivatives having excellent antitumor activity. The compounds of this invention are characterized by having ester (—OCR$_1$), amide (NHCOR$_1$) and sulfonamide (NHSO$_2$R$_4$) linkage with alkyl, aryl, heteroaryl, amino acids or dipeptide groups which were prepared by the common starting compound 2. The preparation of compound 2 was carried out by the synthetic route as described in J. Chem. Soc. Perkin Trans. I 2222, 1980, starting from 4-acetoxyazetidinone.

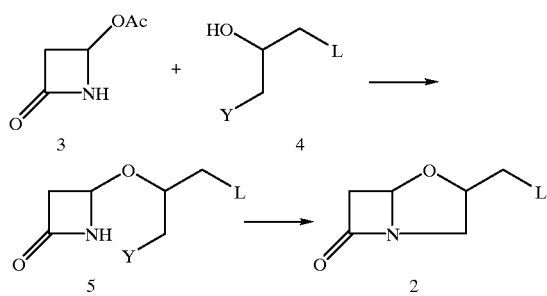

Wherein L and Y are suitably selected from leaving groups such as chlorine, bromine, iodine, methanesulfonyloxy group, trifluoromethanesulfonyloxy group, p-toluenesulfonyloxy group and p-chlorobenzenesulfonyloxy group.

The preparation of substituted aminomethyl-4-oxa-1-azabicyclo[3.2.0]heptan-7-one of general formula I was done by synthetic route as shown below.

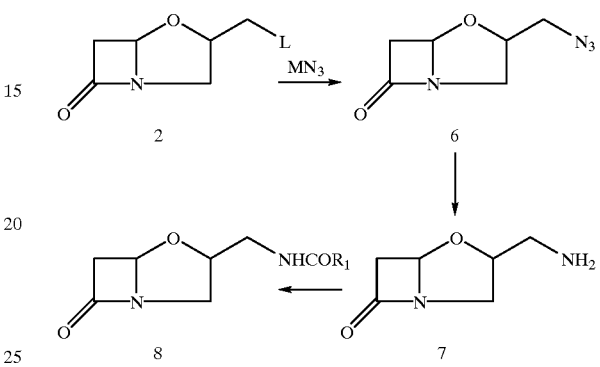

Wherein M is sodium, potassium or trimethylsilyl and R$_1$ is a $C_1$–$C_6$ alkyl group which may be substituted by 1–3 substituents selected from halogen, hydroxy, formyloxy, azido, carboxyl, heteroaryl or acetamide; a $C_2$–$C_4$ alkenyl group; a $C_2$–$C_4$ alkynyl group; a $C_3$–$C_6$ cycloalkyl group; a phenyl group which may be substituted by 1–3 substituents selected from hydroxy, halogen, $C_1$–$C_6$ alkoxy group or cyano; a $C_5$–$C_6$ heteroaryl group; a NR$_2$R$_3$ wherein R$_2$ and R$_3$ are the same or different and each is a hydrogen, $C_1$–$C_6$ alkyl group or (7-oxo-1-aza-4-oxabicyclo[3.2.0]hept-3-yl) methyl group or bezyloxy group.

Certain 3-substituted amidomethyl-4-oxa-1-azabicyclo[3.2.0]heptan-7-one general formula I when substituent of R$_1$ in —COR$_1$ is acetamide, azide, formyloxy, hydroxy and heteroaryl, were prepared by the scheme as shown below.

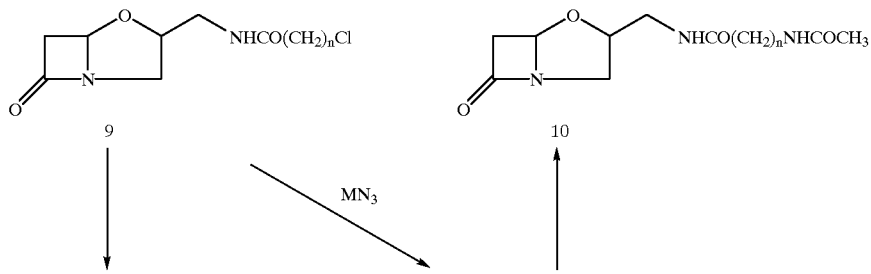

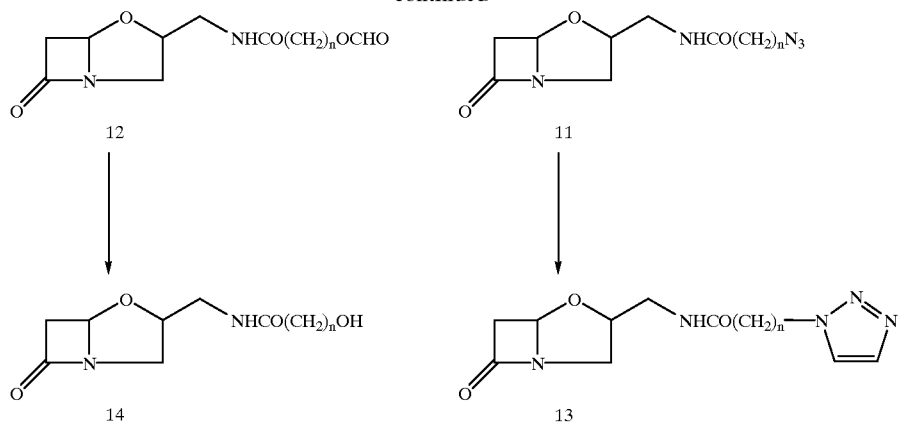

Wherein n is 1 to 5; M is defined as above.

Besides the procedure described above the stereoisomer of 3-acetyaminomethyl-4-oxa-1-azabicyclo[3.2.0]heptan-7-one(8,R=CH₃) were prepared by the scheme as described below starting from 3-hydroxymethyl-4-oxa-1-azabicyclo[3.2.0]heptan-7-one(1).

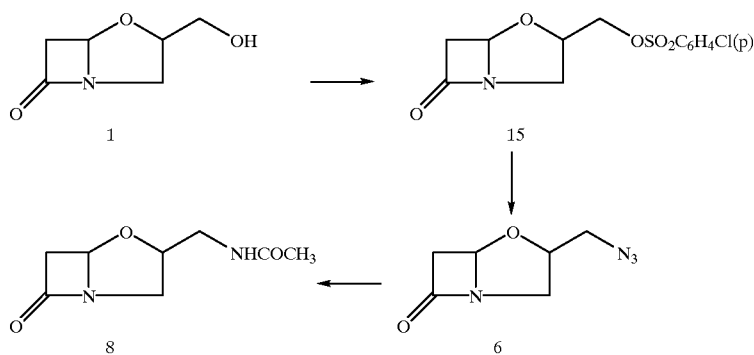

Certain derivatives of formula I wherein X is NH and R is SO₂R₄, were prepared by following the scheme as shown below starting from 3-azidomethyl-4-oxa-1-azabicyclo[3.2.0]heptan-7-one(6).

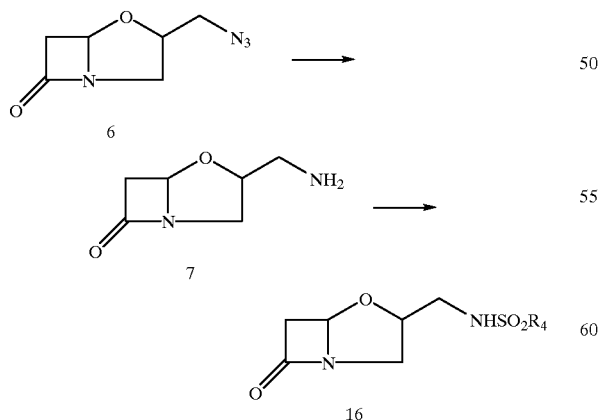

Wherein R₄ is the same as defined above.

The amide derivative of amino acids and dipeptides of general formula I were alternatively prepared by the synthetic scheme as shown below in two steps. In the first step, 3-aminomethyl-4-oxa-1-azabicyclo[3.2.0]heptan-7-one(7) was coupled with either N-protected acid in the presence of dicyclohexylcarbodiimide (DCC) or acid chloride in the presence of a base or activated ester followed by coupling with another N-protected amino acid which may or may not be the same. The resulting compounds were deprotected in the presence of H₂ and Palladium catalyst under pressure or atmospheric pressure.

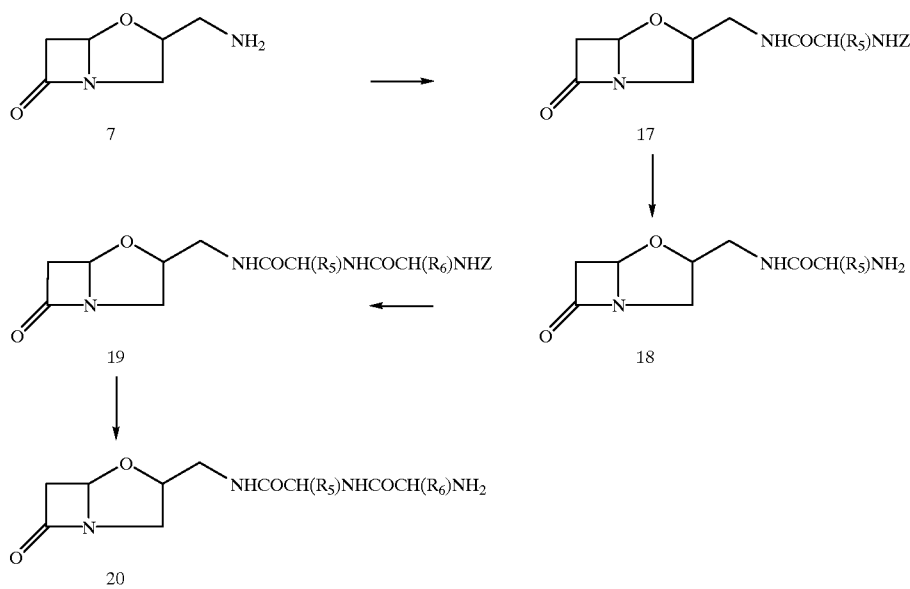

Wherein $R_5$ and $R_6$ are selected from hydrogen, methyl, 1-methylethyl, phenylmethyl, 2-carboxyethyl, carboxymethyl, hydroxymethyl, benzyloxymethyl, acetyloxymethyl, aminobutyl and Z is benzyloxycarbonyl, acetyl, 2-thienylacetyl or tert-butoxycarbonyl.

The ester derivative of amino acids and dipeptides were prepared by the coupling of 3-bromomethyl-4-oxa-1-azabicyclo[3.2.0]heptan-7-one(2) with N-protected aminoacids in the presence of a base. The amine group was deprotected and couples with another molecule of amino acid as shown in the scheme below.

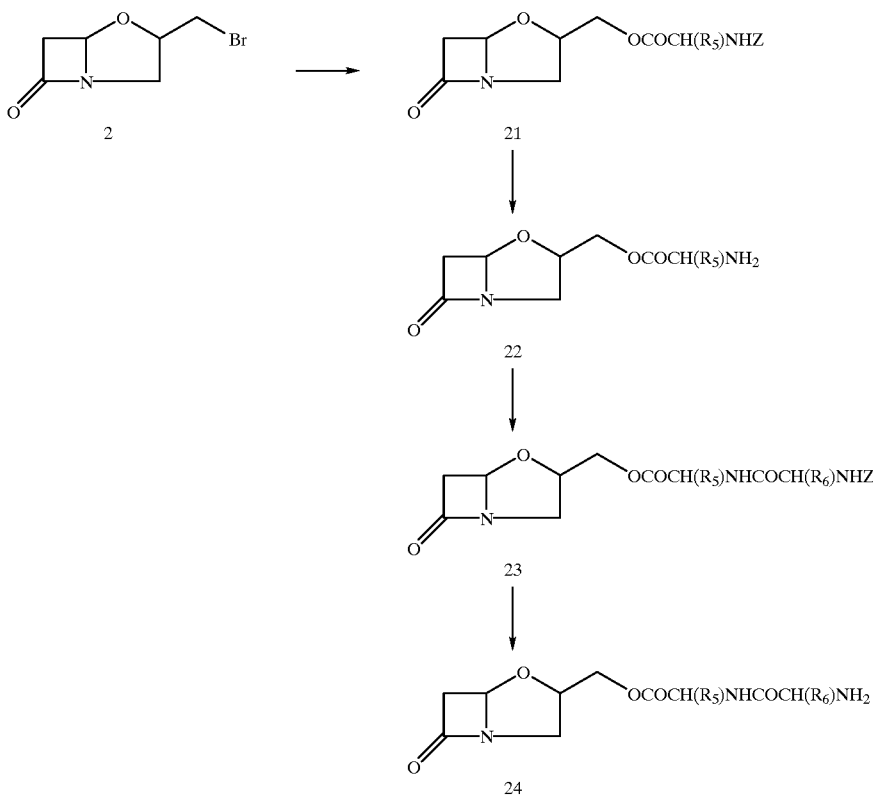

Wherein $R_5$, $R_6$ and Z are defined as above.

In the above descriptions, the reactants are reacted together with solvent at elevated or low temperatures for sufficient time to allow the reaction to proceed to completion. The reaction conditions will depend upon the nature and reactivity of the reactants. Wherever a base is used in a reaction, they are selected from triethylamine, pyridine, 4-dimethylamino-pyridine, diisopropylethylamine, 1,5,-Dizabicyclo[4.3.0]non-5-ene, 1,8-Dizabicyclo[5.4.0]undec-7-ene, sodium carbonate, potassium carbonate or cesium carbonate.

The solvents of choice for the reaction are non reactive solvents such as acetonitrile, tetrahydrofuran, ethanol, methanol, chloroform, ethylacetate, methylene chloride, dimethylformamide, dimethylsulfoxide, hexamethylphosphoric triamide or the like. Solvent mixtures may also be utilized.

Reaction temperatures would generally range from between −70° C. to 140° C. The preferred molar ratio of reactants are 1:1 to 5.0. The reaction time range from 0.5 to 72 hours, depending on the reactants.

The deprotection of N-protective group is carried out either by hydrogenation in the presence of acids, such as hydrochloric acid or acetic acid, or by hydrolysis with appropriate acids, such as hydrochloric acid, trifluoriacetic acid or acetic acid in solvents such as methanol, ethanol, propanol or ethylacetate. The hydrogenation reaction is usually carried out in the presence of a metal catalyst, such as Pd, Pt or Rh, under normal pressure to high pressure.

The compound of the invention, when used as an agent for treating malignant tumors of mammals including humans, may take pharmaceutical dosage forms including parenteral preparations such as injections, suppositories, aerosols and the like, and oral preparations such as tablets, coated tablets, powders, granules, capsules, liquids and the like. Injections are generally preferred. The above preparations are formulated in a manner known in the art.

For the formulation of solid preparations for oral administration, an excipient, and if desired, a binder, disintegrator, lubricant, coloring agent, corrigent, flavor, etc. are added to the compound of the invention, and then tablets, coated tablets, granules, powders, capsules or the like are prepared in a conventional manner.

For the formulation of injections, a pH adjusting agent, buffer, stabilizer, isotonic agents, local anesthetic or the like is added to the active ingredient of the invention, and injections for subcutaneous, intramuscular or intravenous administration can be prepared in a conventional manner.

For the formulation of suppositories, a base, and if desired, a surfactant are added to the active ingredient of the invention, and the suppositories are prepared in a conventional manner.

The excipients useful for the solid preparations for oral administration are those generally used in the art, and useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, schellac, sucrose, water, ethanol, propanol, carboxymethylcellulose, potassium phosphate and the like, lubricants such as magnesium stearate, talc and the like, and further include additives such as usual known coloring agents, disintegrators and the like. Examples of bases useful for the formulation of suppositories are, for example, oleaginous bases such as cacao butter, polyethylene glycol, lanolin, fatty acid triglycerides, Witepsol (trademark, Dynamite Nobel Co., Ltd.) and the like. Liquid preparations may be in the form of aqueous or oleaginous suspension, solution, syrup, elixir and the like, which can be prepared by a conventional way using additives.

The amount of the compound (I) of the invention to be incorporated into the pharmaceutical composition of the invention varies with the dosage form, solubility and chemical properties of the compound, administration route, administration scheme and the like. Preferably the amount is about 1 to 25 w/w % in the case of oral preparations, and about 0.1 to about 5 w/w % in the case of injections which are parenteral preparations.

The dosage of the compound (I) of the invention is suitably determined depending on the individual cases taking symptoms, age and sex of the subject and the like into consideration. Usually, the dosage in the case of oral administration is about 50 to 1000 mg per day for an adult in 2 to 4 divided doses, and the dosage in the case of injection, for example, by intravenous administration is 2 ml (about 1 to 50 mg) which is administered once a day for adults wherein the injection may be diluted with physiological saline or glucose injection liquid if so desired, and slowly administered over at least 5 minutes. The dosage in the case of suppositories is about 1 to 500 mg which is administered once or twice a day at an interval of 6 to 12 hours wherein the suppositories are administered by insertion into the rectum.

REFERENCE EXAMPLE 1

(3R,5S)-3-[(4-Chlorobenzenesulfonyl)oxymethyl]-4-oxa-1-azabicyclo[3.2.0]heptan-7-one A mixture of (3R,5S)-3-Hydroxymethyl-4-oxa-1-azabicyclo[3.2.0]heptan-7-one (790 mg), Triethylamne (726 mg), 4-Chlorobenzenesufonyl chloride (1.51 g) in Dichloromethane was stirred for 16 hrs. The reaction mixture was purified by silicagel column chromatography, using Chloroform-Ethyl acetate (5:1) as eluent and desired sulfonate was obtained as solid.

Yield:84%.

m.p.:153.6–155.1° C., $[\alpha]_D^{25}$=−90.0° (c=0.67, CDCl$_3$).

$^1$H NMR(CDCl$_3$,δ):2.82(1H,d,J=16.1),2.84(1H,dd,J=5.6, 5.9),3.28(1H, ddd,J=1.0,2.9,16.1),3.98(1H,dd, J=7.1,11.7), 4.09(1H,dd,J=4.4, 10.8),4.21 (1H,dd,J=3.6,10.8),4.47–4.58 (1H,m),5.27(1H,d,J=2.6), 7.56(2H,d,J=8.7),7.86(2H,d,J= 8.7).

IR(Nujol,cm$^{-1}$):1776,1450.

REFERENCE EXAMPLE 2

(3S,5S)-3-Azidomethyl-4-oxa-1-azabicyclo[3.2.0]heptan-7-one

The sulfonate of reference example 1 (1.45 g) was treated with Sodium azide (767 mg) in Dimethylformamide (10 ml) at 70° C. for 2.5 hrs. The reaction mixture was diluted with Ethyl acetate, washed with water, brine and dried over Magnesium sulfate. The solvent was removed in vacuo and the residue was purified by silicagel column chromatography using Hexane-Ethyl acetate (2:1) as eluent.

Yield:94% (oil).

$[\alpha]_D^{23}$=−159.0° (c=0.67,CDCl$_3$).

$^1$H NMR(CDCl$_3$,δ):2.84(1H,dd,J=11.7,6.9),2.87(1H,d,J= 16.2),3.26–3.38 (2H,m),3.54(1H,dd,J=3.7,13.2),3.98(1H, dd,J=6.7,11.7),4.43–4.54 (1H,m),5.40(1H,d,J=2.6).

IR(Neat,cm$^{-1}$):2960,2100,1778.

REFERENCE EXAMPLE 3

Allyl[(3RS,5RS)-7-oxo-1-aza-4-oxabicyclo[3.2.0]hept-3-yl]methylamino succinate 300 mg of (3RS,5RS)-3-Azidomethyl-4-oxa-1-azabicyclo[3.2.0]heptan-7-one was hydrogenated with 200 mg of 5% Palladium on activated carbon in 30 ml of Ethyl acetate at 50 psi for 1 hr. After removal of catalyst by filtration, 20 mg(0.21 mmol) of Triethylamine, 360 mg (2.30 mmol) of Allyl hydrogen succinate and 480 mg(2.30 mmol)

of 1,3-Dicyclohexyl carbodiimide were added under ice cooling. The reaction mixture was stirred at room temperature for 4 hrs. The resulted solid was filtered off and the filtrate was concentrated. The residue was purified by silica gel column using Hexane-Ethylacetate (1:1) as eluent. 150 mg of title compound was obtained.

Yield:30%.

$^1$H NMR(CDCl$_3$,δ):2.47–2.96(6H,m),3.25–3.59(3H,m), 3.94(1H,dd;J=6.4, 11.8),4.30–4.42(1H,m),4.57–4.61(2H, m),5.21–5.37(3H,m),5.81–6.04 (2H,m).

IR(Neat,cm$^{-1}$):3330,2955,1783,1736.

EXAMPLE 1

(3RS,5RS)-3-(N-Acetylaminomethyl)-4-oxa-1-azabicyclo[3.2.0]heptan-7-one(1)

2.75 g of (3RS,5RS)-3-Azidomethyl-4-oxa-1-azabicyclo [3.2.0]heptan-7-one, prepared by the known method, was hydrogenated over 1.0 g of 10% Palladium on activated carbon in Ethyl acetate at 50 psi for 1 hr. After removal of catalyst by filteration, 2.3 ml of Triethylamine was added and then 1.2 ml of Acetyl chloride was added dropwise at 5° C. The reaction mixture was then stirred for 2 hrs. The resulting mixture was loaded on flash silicagel column and eluted with Ethyl acetate. The title compound was obtained as white solid.

Yield: 67% m.p.:59–61° C.

$^1$H NMR(CDCl$_3$,δ):2.02(3H,s),2.64(1H,dd,J=6.5,11.7), 2.84(J=16.2), 3.26–3.39(2H,m),3.56(1H,ddd,J=3.6,6.5, 14.3),3.96(1H,dd,J=6.5, 11.9),4.37 (1H,m),5.32(1H,d,J=2, 7),5.80(1H,br.s).

IR(Nujol,cm$^{-1}$):3565,1768,1646,1540.

EXAMPLE 2

(3S,5S)-3-(N-Acetylaminomethyl)-4-oxa-1-azabicyclo[3.2.0]heptan-7-one (2)

(3S,5S)-3-Azidomethyl-4-oxa-1-azabicyclo[3.2.0] heptan-7-one of reference example 2 (710 mg) was hydrogenated in presence of Acetic anhydride (431 mg) in Ethyl acetate (20 ml) at 50 psi for 1 hr. The reaction mixture was purified by silicagel column chromatography using Ethyl acetate-Acetone (5:1) as eluent and the title compound was obtained as solid.

Yield:89%.

m.p.:82.5–84.5° C., [α]$_D^{25}$=–174.0° (c=1.0, CHCl$_3$).

$^1$H NMR(CDCl$_3$,δ):2.02(3H,s),2.68(1H,dd,J=7.0,11.8), 2.84(1H, d, J=16.2),3.26–3.40(2H,m),3.56(1H,ddd,J=3.6, 6.3,14.2),3.96(1H,dd, J=6.4, 11.8),4.31–4.43 (1H,m),5.33 (1H,d,J=2.5),5.86(1H,br.s).

IR(Nujol,cm$^{-1}$):3340,1764,1646,1540.

EXAMPLE 3

(3R,5R)-3-(N-Acetylaminomethyl)-4-oxa-1-azabicyclo[3.2.0]heptan-7-one (3)

According to the similar method as described in reference example 1,2 and example 2, the title compound was obtained from (3S,5R)-3-Hydroxymethyl-4-oxa-1-azabicyclo[3.2.0]heptan-7-one.

Yield: 87%.

m.p.:86.0–87.6° C., [α]$_D^{25}$=+192.0° (c=1.0, CHCl$_3$).

$^1$H NMR(CDCl$_3$,δ):2.02(3H,s),2.68(1H,dd,J=7.0,11.8), 2.84(1H,d, J=16.5),3.26–3.40(2H,m),3.56(1H,ddd,J=3.6, 6.3,14.2),3.96(1H,dd, J=6.4,11.8),4.31–4.43 (1H,m),5.33 (1H,d,J=2.6),5.87(1H,br.s).

IR(Nujol,cm$^{-1}$):3345,1764,1646,1542.

EXAMPLE 4

(3RS,5RS)-3-(N-Hexanoylaminomethyl)-4-oxa-1-azabicyclo[3.2.0]heptan-7-one (4)

According to the same method as described in example 1, the title compound was obtained as solid in example 1.

Yield:41%.

m.p.:56–57° C.

$^1$H NMR(CDCl$_3$,δ):0.90(3H,t,J=6.6),1.27–1.40(4H,m), 1.56–1.71(2H,m), 2.20(2H,t,J=7.9),2.68 (1H,dd,J=7.0,11.8), 2.84(1H,d,J=16.1),3.26–3.42(2H,m),3.55(1H,ddd,J=3.8,6.3, 14.3),3.95(1H,dd,J=6.5,11.8), 4.31–4.43(1H,m),5.32(1H,d, J=2.6),5.87(1H,br.s).

IR(Nujol,cm$^{-1}$):3320,1762,1659,1631.

EXAMPLE 5

(3RS,5RS)-3-[N-(2-Methylpropanoyl)aminomethyl]-4-oxa-1-azabicyclo[3.2.0]heptan-7-one (5)

According to the same method as described in example 1, the title compound was obtained as solid.

Yield:53%.

m.p.:76–77° C.

$^1$H NMR(CDCl$_3$,δ):1.17(6H,d,J=6.9),2.35–2.42(1H,m), 2.67(1H,dd,J=7.0,11.7),2.85(1H,d,J=16.3),3.27–3.42(2H, m),3.51–3.65(1H,m),3.96 (1H,dd,J=6.4,11.8),4.30–4.45 (1H,m),5.32(1H,s),5.75(1H,br.s).

IR(Nujol,cm$^{-1}$):3325,2960,1766.

Anal.:

calcd: C, 56.59; H, 7.60; N, 13.20

Found: C, 56.36; H, 7.79; N, 12.98

EXAMPLE 6

(3RS,5RS)-3-(N-Cyclohexylcarbonylaminomethyl)-4-oxa-1-azabicyclo[3.2.0]heptan-7-one (6)

According to the same method as described in example 1, the title compound was obtained as solid.

m.p.:83–85° C.

Yield:5%.

$^1$H NMR(CDCl$_3$,δ):1.14–1.95(10H,m),2.02–2.20(1H,m), 2.60–2.72(1H,dd, J=6.8,11.7),2.84(1H,d,J=16.2),3.22–3.42 (2H,m),3.46–3.64(1H,m),3.95 (1H,dd,J=6.5,11.8), 4.31–4.43(1H,m),5.33(1H,d,J=2.7)5.68–5.82 (1H,m).

IR(Nujol,cm$^{-1}$):3305,2930,1781.

EXAMPLE 7

(3RS,5RS)-3-[N-(Trifluoroacetyl)aminomethyl]-4-oxa-1-azabicyclo[3.2.0]heptan-7-one(7)

According to the same method as described in example 1, the title compound was obtained as solid.

Yield:74%.

m.p.:54–57° C.

$^1$H NMR(CDCl$_3$,δ):2.78(1H,dd,J=6.7,11.5),2.89(1H,d,J= 16.8),3.30–3.49 2H,m),3.68(1H,ddd,J=3.4,6.5,14.3),4.03 (1H,dd,J=6.5,11.9), 4.37–4.49(1H,m),5.36(1H,d,J=2.7),6.62 (1H,br.s).

IR(Nujol,cm$^{-1}$):3300,1773,1710,1550.

EXAMPLE 8

(3RS,5RS)-3-(N-Chloroacetylaminomethyl)-4-oxa-1-azabicyclo[3.2.0]heptan-7-one (8)

According to the same method as described in example 1, the title compound was obtained as solid.

Yield:51%.

m.p.:65–66.4° C.

$^1$H NMR(CDCl$_3$,δ):2.68(1H,dd,J=6.8,11.7),2.87(1H,d,J=16.0),3.32(1H, dd,J=2.2,16.7),3.43–3.50(1H,m),3.60(1H, ddd,J=3.6,6.2,14.2),3.99 (1H,dd,J=6.5,11.9),4.09(2H,s), 4.36–4.46(1H,m),5.36(1H,d,J=2.6), 6.88(1H,br.s).

IR(Nujol,cm$^{-1}$):3315,1764.

EXAMPLE 9

(3RS,5RS)-3-[N-(Azidoacetyl)aminomethyl]-4-oxa-1-azabicyclo[3.2.0]heptan-7-one (9)

(1) (3RS,5RS)-3-(N-Chloroacetylaminomethyl)-4-oxa-1-azabicyclo[3.2.0]heptan-7-one(500 mg), of example 8, and Sodium azide(297 mg) were stirred in Dimethyl sulfoxide (10 ml) at room temperature for 14 hrs. The reaction mixture was diluted with Ethyl acetate, washed with water, brine and dried over Magnesium sulfate. The residue, which obtained after removal of solvent in vacuo, was purified by silicagel column chromatography (Hexane+Ethyl acetate 1:2). The title compound was obtained as oil.

Yield:89%.

(2) (3RS,5RS)-3-Azidomethyl-4-oxa-1-azabicyclo[3.2.0]heptan-7-one (1.0 g) was hydrogenated with 5% Palladium on activated carbon (250 mg) in Ethyl acetate(20 ml)at 50 psi for 2 hrs. To the reaction mixture, Triethylamine(121 mg), Azidoacetic acid(1.21 g), 1,3-Dicyclohexyl carbodiimide(2.46 g) and Ethyl acetate(10 ml) was added and stirred for 1 hr at room temperature. After removal of solid by filtration, the solvent was removed in vacuo and the residue was purified by silicagel column chromatography (Hexane-Ethyl acetate 1:3). Desired azidoacetamide was obtained as oil.

Yield:52%.

(3) A mixture of (3RS,5SR)-3-Bromomethyl-4-oxa-1-azabicyclo[3.2.0]heptan-7-one (1.0 g), Azidoacetic acid (735 mg), Triethylamine (737 mg) and Hexamethylphosphoric triamide(5 ml) was heated with stirring at 60–70° C. for 24 hrs. The reaction mixture was then diluted with Ethyl acetate, washed with water, brine and dried over Magnesium sulfate. The residual oil after removal of solvent in vacuo, was purified by silicagel column chromatography using Hexane-Ethyl acetate (2:3) as eluent. The desired azidoacetate was obtained as oil.

Yield:36%.

$^1$H NMR(CDCl$_3$,δ):2.81(1H,dd,J=6.3,11.7),2.87(1H,d,J=16.2),3.28 (1H,ddd,J=0.7,2.8,16.2),3.95(2H,s),4.02(1H,dd,J=6.9,11.7),4.29 (2H,d,J=7.8),4.53–4.65 (1H,m),5.35(1H,d,J=2.7).

IR(Neat,cm$^{-1}$):2115,1784,1751,1193.

EXAMPLE 10

(3RS,5RS)-3-[N-(1,2,3-Triazole-1-yl)acetylaminomethyl]-4-oxa-1-azabicyclo[3.2.0]heptan-7-one (10)

150 mg of (3RS,5RS)-3-[N-(Azidoacetyl)aminomethyl]-4-oxa-1-azabicyclo[3.2.0]heptan-7-one was dissolved in 10 ml of Acetone and Acetylene was bubbled at −78° C. for 5 minutes. The reaction mixture was heated at 60–70° C. in seal tube for 17 hrs. After reaction completed, solvent was removed in vacuo and the residue was purified by silicagel column chromatography (Ethyl acetate+Acetone 3:1). The title compound was obtained as oil.

Yield:69%.

$^1$H NMR(CDCl$_3$,δ):2.57(1H,dd,J=6.9,11.7),2.82(1H,d,J=16.0),3.28 (1H,dd,J=2.9,16.8),3.40–3.51(2H,m),3.94(1H, dd,J=6.5,11.9),4.29–4.41(1H,m),5.12(2H,s),5.24(1H,d,J=2.6),7.73(1H,d,J=0.8),7.80 (1H,d,J=0.7)

IR(Neat,cm$^{-1}$):3310,1779,1689,1555.

EXAMPLE 11

(3RS,5RS)-3-[N-(Formyloxyacetyl)aminomethyl]-4-oxa-1-azabicyclo[3.2.0]heptan-7-one (11)

A mixture of (3RS,5RS)-3-(N-Chloroacetylaminomethyl)-4-oxa-1-azabicyclo[3.2.0]heptan-7-one(260 mg), Sodium formate(97 mg) in Dimethyl sulfoxide(5 ml) was stirred at room temperature for 15 hrs, then 70° C. for 3days. The reaction mixture was poured into water, extracted with Chloroform and dried over Magnesium sulfate. The residue which obtained after removal of solvent in vacuo, was purified by flash chromatography (Ethyl acetate). The title compound was obtained as oil.

Yield:33%.

$^1$H NMR(CDCl$_3$,δ):2.68(1H,dd,J=6.7,11.6),2.86(1H,d,J=15.9),3.27–3.47 (2H,m),3.64 (1H,ddd,J=3.5,6.4,14.2), 4.34–4.46(1H,m),4.69 (2H,s),5.34(1H,d,J=2.6),6.48(1H, br.s),8.16(1H,s).

IR(Neat,cm$^{-1}$):3315,1770,1719,1667,1537.

EXAMPLE 12

(3RS,5RS)-3-[N-(Hydroxyacetyl)aminomethyl]-4-oxa-1-azabicyclo[3.2.0]heptan-7-one(12)

To a solution of (3RS,5RS)-3-[N-(Formyloxyacetyl)aminomethyl]-4-oxa-1-azabicyclo[3.2.0]heptan-7-one(55 mg) in a mixture of Methanol(1 ml) and water (0.1 ml), Sodium hydrogenecatbonate(20 mg) was added and stirred at room temperature for 10 minutes. Reaction mixture was loaded directly on flash column and eluted with Ethyl acetate+Acetone (1:2). The title compound was obtained as solid.

Yield: 69%.

m.p.:103–105° C.

$^1$H NMR(CDCl$_3$,δ):2.54(1H,t,J=5.1),2.70(1H,dd,J=7.4,12.2),3.31(1H, dd,J=2.2,15.9),3.44(1H,dd,J=7.8,14.2),3.60 (1H,ddd,J=3.8,6.3,14.2), 3.98(1H,dd,J=6.5,11.8),4.16(2H,d,J=5.1),4.35–4.47(1H,m),5.35 (1H,d,J=2.6),6.80 (1H,br.s).

IR(Nujol,cm$^{-1}$):3330,1769,1650,1531.

EXAMPLE 13

(3RS,5RS)-3-[N-(6-Bromohexanoyl)aminomethyl]-4-oxa-1-azabicyclo[3.2.0]heptan-7-one (13)

According to the same method as described in example 1, the title compound was obtained as oil.

Yield:50%.

$^1$H NMR(CDCl$_3$,δ):1.50–2.40(8H,m),2.67(1H,dd,J=6.9,11.7),2.85 (1H,d,J=16.1),3.38–3.76(5H,m),3.96(1H,dd,J=6.4,11.8),4.43–4.56 (1H,m),5.33(1H,d,J=2.6),5.80–5.93 (1H,m).

IR(Neat,cm$^{-1}$):3310,1772,1639.

EXAMPLE 14

(3RS,5RS)-3-[N-(6-Formyloxyhexanoyl)aminomethyl]-4-oxa-1-azabicyclo[3.2.0]heptan-7-one (14)

According to the same method as described in example 11, the title compound was obtained as solid.

Yield:25%.

m.p.:61.5–63° C.

¹H NMR(CDCl₃,δ):1.37–1.81(6H,m),2.22(2H,t,J=7.5), 2.67(1H,dd, J=7.0,11.7),2.85(1H,d,J=16.2),3.28–3.65(3H, m),3.96(1H,dd, J=6.4,11.8),4.17(2H,t,J=6.6),4.32–4.42(1H, m),5.32 (1H,d,J=2.6), 5.74(1H br.s),8.06(1H,s).

IR(Nujol,cm⁻¹):3315,1783,1715.

EXAMPLE 15

(3RS,5RS)-3-[N-(6-Azidohexanoyl)aminomethyl]-4-oxa-1-azabicyclo[3.2.0]heptan-7-one (15)

According to the same method as described in example 9, the title compound was obtained as oil.

Yield:70%.

¹H NMR(CDCl₃,δ):1.33–2.30(7H,m),2.62–2.72(1H,dd, J=6.7,11.7),2.84 (1H,d,J=16.0),3.22–3.65(5H,m),5.92(1H, dd,J=6.5.11.8),4.30–4.45 (1H,m),5.32(1H,d,J=2.6), 5.73–5.85(1H,m).

IR(Neat,cm⁻¹):3310,2935,1772,1639.

EXAMPLE 16

(3RS,5RS)-3-[N-[(1,2,3-Triazol-1-yl)hexanoyl]aminomethyl]-4-oxa-1-azabicyclo[3.2.0]heptan-7-one (16)

According to the same method as described in example 10, the title compound was obtained as solid.

Yield:37%.

m.p.:108–109° C.

¹H NMR(CDCl₃,δ):1.24–2.04(6H,m),2.21(2H,t,J=7.3), 2.65(1H,dd,J=7.2, 11.9),2.83(1H,d,J=16.3),3.24–3.61(3H, m),3.94(1H,dd,J=6.4,11.8), 4.30–4.46(3H,m),5.31(1H,d,J=2.6),5.74–5.87(1H,m),7.55(1H,s),7.71 (1H,s).

IR(Nujol,cm⁻¹):3315,2945,1783,1715.

EXAMPLE 17

(3RS,5RS)-3-[N-(6-Acetylaminohexanoyl)aminomethyl]-4-oxa-1-azabicyclo[3.2.0]heptan-7-one (17)

According to the same method as described in example 10, the title compound was obtained as solid.

Yield:10%.

m.p.:117–118° C.

¹H NMR(CDCl₃,δ):1.33–1.76(6H,m),1.97(3H,s),2.21 (2H,t,J=7.2),2.68 (1H,dd J=7.0,11.9),2.86(1H,d,J=16.3), 3.21–3.66(5H,m),3.98(1H,dd, J=6.4,11.8),4.30–4.43(1H, m),5.32(1H,d,J=2.7),5.52–5.65(1H,m), 5.78–5.92(1H,m).

IR(Nujol,cm⁻¹):3275,1776,1634.

EXAMPLE 18

Sodium{N-[(3RS,5RS)-7-oxo-1-aza-4-oxabicyclo [3.2.0]hept-3-yl]methylamino}succinate(18)

The protected compound obtained in reference example 3 was dissolved in a mixture of Ethyl acetate and Dichloromethane (1:1, 4 ml) and Sodium 2-ethylhexanoate(0.30 ml), Triphenylphosphine (13 mg), and Tetrakis (triphenylphosphine)palladium(0) (22 mg) were added. The reaction mixture was stirred at room temperature for 2 hrs and solid was collected by suction. Solid was washed with Acetonitrile and dried. 65 mg of the title compound was obtained as white solid.

Yield:46%.

m.p.:100° C.(dec.).

1H NMR(DMSO-d₆,δ):2.08–2.25(4H,m),2.61–2.81(2H, m),3.11–3.36(3H, m), 3.76(1H,dd,J=6.6,11.5),4.27–4.33 (1H,m),5.33 (1H,d,J=2.5),8.86–8.98 (1H,m).

IR(Nujol,cm−1):3330,1781,1651

EXAMPLE 19

(3RS,5RS)-3-[N-(4-Pentenoyl)aminomethyl]-4-oxa-1-azabicyclo[3.2.0]heptan-7-one (19)

600 mg of (3RS,5RS)-3-Azidomethyl-4-oxa-1-azabicyclo[3.2.0]heptan-7-one was hydrogenated with 1.0 g of 10% Palladium on activated carbon in Ethyl acetate at 50 psi for 1 hr. After removal of catalyst by filtration, 360 mg (3.6 mmol) of 4-Pentenoic acid and 300 mg (1.8 mmol) of 1,3-Dicyclohexyl carbodiimide were added under ice-cooling. The reaction mixture was then stirred at room temperature for 2 hrs. Resulted solid was filtered off and the filtrate was concentrated in vacuo. The residue was purified by flash silicagel column using Hexane-Ethyl acetate (1:1) as eluent and the title compound was obtained as oil.

Yield:15%.

¹H NMR(CDCl₃,δ):2.25–2.48(4H,m),2.66(1H,dd,J=7.5, 11.7),2.84(1H,d, J=16.0),3.25–3.43(2H,m),3.48–3.64(1H, m),3.97(1H,dd,J=6.5,11.8), 4.31–4.44(1H,m),4.98–5.14 (2H,m),5.33(1H,d,J=2.6),5.75–5.92(2H,m).

IR(Neat,cm⁻¹):3275,1776,1634.

EXAMPLE 20

(3RS,5RS)-3-[N-Propynoylaminomethyl]-4-oxa-1-azabicyclo[3.2.0]heptan-7-one (20)

According to the same method as described in example 19, the title compound was obtained as solid.

Yield:29%.

m.p.:76.5–78° C.

¹H NMR(CDCl₃,δ):2.68(1H,dd,J=5.3,10.0),2.87(1H,s), 2.88(1H,d, J=10.5),3.33(1H,d,J=11.1),3.63(1H,ddd,J=2.6, 4.7,10.0),3.99(1H,dd, J=4.7,7.9),4.36–4.44 (1H,m),5.35 (1H,d,J=2.1),6.20(1H,br.s).

IR(Nujol,cm⁻¹):3270,2115,1782,1657.

EXAMPLE 21

(3RS,5RS)-3-[N-(Benzyloxycarbonyl)aminomethyl]-4-oxa-1-azabicyclo[3.2.0]heptan-7-one (21)

According to the same method as described in example 1, the title compound was obtained as oil.

Yield:54%.

¹H NMR(CDCl₃,δ):2.70(1H,dd,J=6.8,12.3),2.86(1H,d,J= 16.6),3.22–3.55(1H,m),3.96(1H,dd,J=5.1,11.5),4.31–4.47 (1H,m),5.06(1H,br.s), 5.10(2H,s),5.31(1H,d,J=2.6).

EXAMPLE 22

(3RS,5RS)-3-aminomethyl-4-oxa-1-azabicyclo [3.2.0]heptan-7-one hydrochloride (22)

890 mg of (3RS,5RS)-3-Azidomethyl-4-oxa-1-azabicyclo[3.2.0]heptan-7-one was hydrogenated as described in example 1. After removal of catalyst by filtration, 5 ml of 1N-HCl was added at −78° C. Water layer was then separated and lyophilized. The title compound was obtained as pale yellow solid.

Yield:73%.

¹H NMR(CDCl₃,δ):2.78–2.86(1H,m),2.82(1H,d,J=15.6), 2.98(1H,d,J=6.12),3.99(1H,d,J=15.6),3.87(1H,dd,J=6.7, 11.7),4.54–4.57(1H,m), 5.38(1H,dd,J=2.6),8.38(2H,br.s).

IR(Nujol,cm−1):3325,1806,1775.

EXAMPLE 23

(3RS,5RS)-3-(N-Benzoylaminomethyl)-4-oxa-1-azabicyclo[3.2.0]heptan-7-one (23)

According to the same method as described in example 1, the title compound was obtained as solid.

Yield: 53%.

m.p.:115–116° C.

¹H NMR(CDCl₃,δ):2.76(1H,dd,J=7.3,11.6),2.86(1H,d,J=16.7),3.31(1H, dd,J=2.9,16.8),3.49–3.62(1H,m),3.78(1H, ddd,J=3.5,6.4,14.2),4.02 (1H,dd,J=6.4,11.8),4.42–4.55(1H, m),5.36(1H,d,J=2.7),6.46(1H, br.s),7.40–7.57(3H,m),7.76–7.81(2H,m).

IR(Nujol,cm⁻¹):3335,1779,1639,1534.

Anal.:

calcd: C, 63.40; H, 5.73; N, 11.38

Found: C, 63.39; H, 5.69; N, 11.25

EXAMPLE 24

(3RS,5RS)-3-[N-(4-Hydroxybenzoyl)aminomethyl]-4-oxa-1-azabicyclo[3.2.0]heptan-7-one (24)

According to the same method as described in example 19, the title compound was obtained as oil.

Yield:25%.

¹H NMR(CDCl₃,δ):2.76(1H,dd,J=6.2,11.5),2.79(1H,d,J=16.3),3.29–3.55(3H,m),3.80(1H,dd,J=6.6,11.5),4.41–4.47(1H,m),5.33(1H,d,J=2.5),6.79(2H,d,J=8.7),7.72(2H,d,J=8.7),8.37(1H,br.s),9.97(1H,s).

IR(Nujol,cm⁻¹):3315,1765,1600.

EXAMPLE 25

(3RS,5RS)-3-[N-(4-Methoxybenzoyl)aminomethyl]-4-oxa-1-azabicyclo[3.2.0]heptan-7-one (25)

According to the same method as described in example 1, the title compound was obtained as solid.

Yield:23%.

m.p.:142.6° C.

¹H NMR(CDCl₃,δ):2.75(1H,dd,J=7.4,12.2),2.86(1H,d,J=16.7),3.31(1H, dd,J=2.9,15.9),3.47–3.61(1H,m),3.76(1H, ddd,J=3.6,6.4,14.3),3.86 (3H,s),4.01(1,dd,J=6.5,11.9),4.42–4.54(1H,m),5.36(1H,d,J=2.7), 6.35(1H,br.s),6.94(2H, d,J=8.8),7.75(2H,d,J=8.9).

IR(Nujol,cm⁻¹):3290,1774,1625.

EXAMPLE 26

(3RS,5RS)-3-[N-(3,4-Dimethoxybenzoyl) aminomethyl]-4-oxa-1-azabicyclo[3.2.0]heptan-7-one (26)

According to the same method as described in example 1, the title compound was obtained as solid.

Yield:45%.

m.p.:170–190° C. (dec.).

¹H NMR(CDCl₃,δ):2.76(1H,dd,J=7.0,11.8),2.89(1H,d,J=9.1),3.32(1H, dd,J=2.4, 16.5),3.52–3.81(2H,m),3.93(3H,s),3.94(3H,s),4.02(1H,dd, J=6.5,11.9),4.46–4.51(1H,m),5.36 (1H,d,J=2.6),6.38(1H,br.s),6.87 (1H,d,J=8.3),7.26–7.31(1H, m),7.43(1H,d,J=2.0).

IR(Nujol,cm⁻¹):3370,2850,1794,1774.

EXAMPLE 27

(3RS,5RS)-3-[N-(4-Fluorobenzoyl)aminomethyl]-4-oxa-1-azabicyclo[3.2.0]heptan-7-one (27)

According to the same method as described in example 1, the title compound was obtained as oil.

Yield:16%.

¹H NMR(CDCl₃,δ):2.67(1H,dd,J=6.9,11.7),2.78(1H,d,J=16.6),3.23(1H, dd,J=2.8,16.6),3.39–3.52(2H,m),3.67(1H, ddd,J=3.7,6.3,14.3),3.93 (1H,dd,J=6.5,11.9),4.35–4.46(1H, m),5.28(1H,d,J=2.6),6.56(1H, br.s),7.00–7.08(2H,m),7.69 (2H,m).

IR(Nujol,cm⁻¹):3345,2965,1783.

EXAMPLE 28

(3RS,5RS)-3-[N-(2,5-Difluorobenzoyl) aminomethyl]-4-oxa-1-azabicyclo[3.2.0]heptan-7-one (28)

According to the same method as described in example 1, the title compound was obtained as solid.

Yield:43%.

m.p.:88.8–90.7° C.

¹H NMR(CDCl₃,δ):2.76(1H,dd,J=7.1,11.8),2.87(1H,d,J=16.4),3.32(1H, dd,J=2.6,16.3),3.57–3.80(2H,m),4.02(1H, dd,J=6.5,11.8),4.44–4.56 (1H,m),5.38(1H,d,J=2.6),7.06–7.20(3H,m),7.42(1H,m).

IR(Nujol,cm⁻¹):3340,2935,1776.

Anal.:

calcd: C, 55.30; H, 4.29; N, 9.93

Found: C, 55.05; H, 4.18; N, 9.74

EXAMPLE 29

(3RS,5RS)-3-[N-(2,4,5-Trifluorobenzoyl) aminomethyl]-4-oxa-1-azabicyclo[3.2.0]heptan-7-one (29)

According to the same method as described in example 1, the title compound was obtained as solid.

Yield:45%.

m.p.:76.5–78.1° C.

¹H NMR(CDCl₃,δ):2.74(1H,dd,J=7.1,11.8),2.87(1H,d,J=16.3),3.33(1H, d,J=16.4),3.57–3.72(2H,m),4.02(1H,dd,J=6.5,11.8),4.67–4.52(1H,m), 5.38 (1H,s),6.96–7.09(2H,m),7.89–8.02(1H,m).

IR(Nujol,cm⁻¹):3300,2960,1786.

Anal.:

calcd: C, 52.01; H, 3.69; N, 9.33

Found: C, 51.79; H, 3.49; N, 9.15

EXAMPLE 30

(3RS,5RS)-3-[N-(4-Cyanobenzoyl)aminomethyl]-4-oxa-1-azabicyclo[3.2.0]heptan-7-one (30)

According to the same method as described in example 1, the title compound was obtained as solid.

Yield:45%.

m.p.:130–170° C.(dec.).

¹H NMR(CDCl₃,δ):2.74(1H,dd,J=6.9,11.8),2.86(1H,d,J=16.5),3.26(1H, dd,J=2.9,16.7),3.46–3.60(1H,m),3.80(1H, ddd,J=3.5,6.4,14.2),4.03 (1H,dd,J=6.4,11.8),4.43–4.55(1H, m),5.37(1H,d,J=2.6),6.65(1H, br.s),7.75(2H,d,J=8.5),7.90 (2H,d,J=8.5).

IR(Nujol,cm⁻¹):3360,2235,1795,1774.

EXAMPLE 31

(3RS,5RS)-3-[N-(Thiophen-2-yl) acetylaminomethyl]-4-oxa-1-azabicyclo[3.2.0] heptan-7-one (31)

500 mg (3.0 mmol) of (3RS,5RS)-3-Azidomethyl-4-oxa-1-azabicyclo[3.2.0]heptan-7-one was hydrogenated as usual manner. The solution was filtered through celite and to the filtrate 0.8 ml of Triethylamine was added. Under cooling, Thiophen-2-yl-acetyl chloride, prepared from 1.0 g of Thiophen-2-yl-acetic acid, was slowly added to it and the mixture was stirred at room temperature for 1 hr. The solution was filtered through silica gel column and the title compound was obtained as oil.

Yield:18%.

$^1$H NMR(CDCl$_3$,δ):2.63(1H,dd,J=7.26),2.80(1H,d,J=16.2),3.26(1H,dd, J=2.3,16.0),3.40–3.48(2H,m),3.81(2H,s), 3.92(1H,dd,J=6.5,11.9), 4.28–4.40(1H,m),5.16(1H,d,J=2.6), 5.88(1H,br.s),6.93–7.04 (2H,m),7.23–7.30(1H,m).

IR(Nujol,cm$^{-1}$):3310, 1767, 1644.

EXAMPLE 32

(3RS,5RS)-3-[N-[(Pyridin-3-yl)carbonyl] aminomethyl]-4-oxa-1-azabicyclo[3.2.0]heptan-7-one (32)

According to the same method as described in example 19, the title compound was obtained as oil.

Yield:7%.

$^1$H NMR(CDCl$_3$,δ):2.75(1H,dd,J=6.9,11.8),2.88(1H,d,J=16.2),3.34 (1H,dd,J=2.2,16.0),3.46–3.63(1H,m),3.82(1H, ddd,J=3.4,6.4,14.3), 4.04(1H, dd,J=6.4,11.9),4.44–4.56(1H, m),5.38(1H,d,J=2.7),6.54 (1H,br.s), 7.43(1H,dd,J=4.8,7.7), 8.15(1H,dt,J=2.2,7.8),8.78 (1H,dd,J=1.6,4.9),9.00(1H,d,J=1.8).

EXAMPLE 33

(3RS,5RS)-3-[N-(N,N-Diethylcarbamyl)] aminomethyl-4-oxa-1-azabicyclo[3.2.0]heptan-7-one (33)

According to the same method as described in example 1, the title compound was obtained as oil.

Yield: 31%.

$^1$H NMR(CDCl$_3$,δ):1.13(6H,t,J=7.2),2.72(1H,dd,J=7.2, 12.0),2.84 (1H, dd,J=16.0),3.21–3.34(3H,m),3.54(1H,ddd, J=3.6,6.3,1.3),3.95(1H, dd,J=6.5,11.8),4.34–4.46(1H,m), 4.46(1H,br.s),5.31(1H,d,J=2.7).

IR(Neat,cm$^{-1}$):3355,1780,1629.

EXAMPLE 34

N,N'-Di-{[(3RS,5RS)-7-oxo-1-aza-4-oxabicyclo [3.2.0]hept-3-yl]methyl}urea (34)

A solution of 340 mg(2.0 mmol) of (3RS,5RS)-3-Azidomethyl-4-oxa-1-azabicyclo[3.2.0]heptan-7-one in 30 ml of Ethyl acetate was hydrogenated under 45 psi with 150 mg of 10% Palladium on activated carbon. The reaction mixture was filtered through celite and concentrated to 15 ml at cool temperature. At this point, Phosgene (20% in Toluene, 260 mg, 2 mmol) was added dropwise while the pH of the mixture was kept at 7 by adding of a saturated solution of K$_2$CO$_3$. The reaction mixture was extracted with Ethyl acetate (3×20 ml) and the combined organic layer was dried over MgSO$_4$ and concentrated. Crystallization of the yellow residue in Ethyl acetate gave product as a white prisms.

Yield:42%.

m.p.: >300° C.(dec.).

$^1$H NMR (DMSO-d$_6$,δ):2.64(2H,dd,J=6.4,11.5),2.77(2H, d,J=16.3),3.18 (4H,t,J=5.4),3.33(2H,dd,J=2.7,16.2), 4.22–4.34(2H, m),5.30(2H,d, J=2.6),6.15(2H,br.t,J=5.8).

IR(Nujol,cm$^{-1}$):3320,1770.

EXAMPLE 35

(3RS,5RS)-3-(N-Methanesulfonylaminomethyl)-4-oxa-1-azabicyclo[3.2.0]heptan-7-one (35)

According to the same method as described in example 1, the title compound was obtained as solid.

Yield:23%.

m.p.:115–190° C. (gradually dec.).

$^1$H NMR(CDCl$_3$,δ):2.82(1H,dd,J=7.5,11.8),2.87(1H,d,J=16.8),3.01 (3H,s),3.22–3.67(3H,m),4.00(1H,dd,J=6.4,11.9), 4.35–4.49(1H,m), 4.58(1H,br.s),5.35(1H,d,J=2.8).

IR(Nujol,cm$^{-1}$):3235,1783,1302.

EXAMPLE 36

(3RS,5RS)-3-[N-(4-Toluenesulfonyl)aminomethyl]-4-oxa-1-azabicyclo[3.2.0]heptan-7-one (36)

According to the same method as described in example 1, the title compound was obtained as solid.

Yield:74%.

m.p.:123–125° C.

$^1$H NMR(CDCl$_3$,δ):2.44(3H,s),2.74(1H,dd,J=11.6,7.4), 2.81(1H,d,J=15.8),2.97–3.21(2H,m),3.28(1H,dd,J=2.2, 15.9),3.01(1H,dd,J=11.9, 17.3),4.26–4.38(1H,m),4.78(1H, br.t,J=6.3),5.26(1H,d,J=2.6),7.33 (2H,d,J=8.1),7.74(2H,d,J=8.3).

IR(Nujol,cm$^{-1}$):3275,1778,1153.

EXAMPLE 37

(3RS,5RS)-3-[N-(4-Chlorobenzenesulfonyl) aminomethyl]-4-oxa-1-azabicyclo[3.2.0]heptan-7-one (37)

According to the same method as described in example 1, the title compound was obtained as solid.

Yield:35%.

m.p.:101–103° C.

$^1$H NMR(CDCl$_3$,δ):2.78(1H,dd,J=7.4,11.6),2.82(1H,d,J=15.9),2.99–3.23(2H,m),3.29(1H,dd,J=6.5,11.9),4.28–4.40 (1H,m),4.89(1H,br.t, J=6.4),5.27(1H,d,J=2.7),7.51(2H,d,J=8.7),7.80(2H,d,J=8.7).

IR(Nujol,cm$^{-1}$):3275,1764,1320,1153.

EXAMPLE 38

(3RS,5RS)-3-N-(4-Methoxybenzenesulfonyl) aminomethyl-4-oxa-1-azabicyclo[3.2.0]heptan-7-one (38)

According to the same method as described in example 1, the title compound was obtained as solid.

Yield:66%.

m.p.:116.5–118.5° C.

$^1$H NMR(CDCl$_3$,δ):2.79(1H,dd,J=5.3,7.3),2.80(1H,d,J=16.0),2.96–3.21 (3H,m),3.27(1H,dd,J=2.5,16.7),3.88(3H,s), 3.92(1H,dd,J=5.4,6.5), 4.24–4.38(1H,m),4.89(1H,br.t,J=6.4),5.26(1H,d,J=2.6),6.99(2H,d,J=8.9),7.79(2H,d,J=8.9).

IR(Nujol,cm$^{-1}$):3265,1770,1578,1489.

EXAMPLE 39

(3RS,5SR)-3-(Aminoacetyl)oxymethyl-4-oxa-1-azabicyclo[3.2.0]heptan-7-one hydrochloride (39)

Azidoacetate(390 mg) obtained in example 9, 5% Palladium on activated carbon(390 mg) were shaken in Ethanol-Ethyl acetate(10 ml each) at 50 psi for 1 hr. After the reaction, catalyst was removed by filtration and 1.5 ml of 1N-HCl was added under cooling condition. Reaction mixture was purified on HP-20 column by elution with water. The title compound was obtained after lyophylization as solid.

Yield:46%.

m.p.:85–110° C.(dec.).

$^1$H NMR (DMSO-d$_6$,δ):2.76–2.88(1H,m),2.80(1H.d,J= 16.3),2.98(1H,d,J=9.4),3.83–4.28(6H,m),4.57–4.83(1H,m), 5.36(1H,d,J=2.5),7.66(1H, br.s),8.43 (2H,br.s).

IR(Nujol,cm$^{-1}$):3205,1751,1651.

EXAMPLE 40

(3RS,5SR)-3-[N-(N-Benzyloxycarbonylaminoacetyl)aminoacetyl] oxymethyl-4-oxa-1-azabicyclo[3.2.0]heptan-7-one (40A) and (3RS,5SR)-3-[N-(Aminoacetyl) aminoacetyl]oxymethyl-4-oxa-1-azabicyclo[3.2.0] heptan-7-one hydrochloride(40B)

A mixture of (3RS,5SR)-3-Bromomethyl-4-oxa-1-azabicyclo[3.2.0]heptan-7-one (2.0 g,9.71 mmol), N-(benzyloxycarbonylaminoacetyl)aminoacetic acid (2.6 g,11.6 mmol) and Cesium carbonate (3.8 g, 11.6 mmol) in Hexamethylphosphoric triamide (15 ml) was stirred at 65–70° C. for 2 hrs. Resulting mixture was poured onto ice-water and extracted with Ethyl acetate. The extract was washed with water, brine and dried over Magnesium sulfate. Solvent was removed in vacuo and the residue was purified on a silica gel column chromatography using ethyl acetate-acetone (9:1) as the eluent gave an off-white solid (40A).

Yield:3.0 g (79%).

$^1$H NMR (DMSO-d$_6$,δ):2.70–2.85(2H,m),3.30(1H,dd,J= 16.1,2.4),3.62–4.20 (7H,m),4.48–4.62(1H,m),5.11(2H,s), 5.32(1H,d,J=2.5),7.35(5H,s),7.55 (1H,t,J=5.7),8.35(1H,t,J= 5.7).

IR(Nujol,cm$^{-1}$):3461,3405,1781,1750,1722,1636.

N-(benzyloxycarbonylaminoacetyl)aminoacetoxy derivative, obtained above (1.1 g,2.81 mmol) and Palladium on activated carbon (10%, 53.8% moist, 0.8 g) in Methanol (140 ml) was shaken at 50 psi for 1 hr under Hydrogen atmosphere. After the reaction, catalyst was filtered off using celite pad. The filtrate was concentrated in vacuo and the residue was re-dissolved in Ethyl acetate. Acidification (1N HCl 2.4 ml, water 26 ml) and followed by freeze-drying gave a solid (40B).

Yield:660 mg(80%).

$^1$H NMR(DMSO-d$_6$,δ):2.62–2.76(2H,m),3.10–4.14(8H, m),4.44–4.55(1H,m), 5.27(1H,d,J=2.5Hz),8.23(3H.br.s), 8.94(1H,t,J=5.7).

IR(Nujol,cm$^{-1}$):3125,1774,1748,1682,1618.

EXAMPLE 41

(3RS,5SR)-3-[N-(L-2-N-Benzyloxycarbonylaminopropanoyl)aminoacetyl] oxymethyl-4-oxa-1-azabicyclo[3.2.0]heptan-7-one (41A) and (3RS,5SR)-3-[N-(L-2-Aminopropanoyl) aminoacetyl]oxymethyl-4-oxa-1-azabicyclo[3.2.0] heptan-7-one hydrochloride(41B)

A solution of (3RS,5SR)-3-[N-(Benzyloxycarbonyl) aminoacetyl]oxymethyl-4-oxa-1-azabicyclo[3.2.0]heptan-7-one (1.0 g,2.99 mmol) in Ethyl acetate (80 ml) was hydrogenolysed at 50 psi for 15 hr using Palladium on activated carbon (10%,53.8% moist,0.75 g). The mixture was filtered through a pad of celite and cooled in an ice-bath. 1,3-Dicyclohexyl carbodiimide (740 mg,3.58 mmol) was added to an ice-cold solution of N-Benzyloxycarbonyl-L-2-aminopropanoic acid (1.33 g,5.98 mmol) in Ethyl acetate (80 ml) and the mixture was stirred for 1 hr. The N-Benzyloxycarbonyl-L-2-aminopropanoic acid-DCC complex was added to the ice-cold Ethyl acetate solution of the amine prepared above. The mixture was stirred at room temperature overnight. The precipitated urea was filtered off, the filtrate was concentrated and passed through a silica gel column using Ethyl acetate as the eluent to give a thick oil (41A).

Yield:83%.

$^1$H NMR(CDCl$_3$,δ):1.40(3H,d,J=7.1),2.74–2.88(2H,m), 3.29(1H,dd,J=16.4, 2.7),3.93–4.60(6H,m),5.11(2H,m), 5.29–5.41(2H,m),5.35(1H,br.s), 6.74(1H,br.s),7.34(5H,s).

(N-protected aminopropanoyl)aminoacetyl ester derivative was deprotected as same manner described in example 40 and the title compound(41B) was obtained as solid.

Yield:720 mg(63%).

$^1$H NMR(DMSO-d$_6$,δ):1.41(3H,d,J=6.9),2.75–2.83(2H, m),3.31(1H),3.81–4.24(6H,m),4.55(1H,m),5.34(1H,d,J= 2.4),8.39(3H,br.s),9.12(1H,br.s).

IR(Nujol,cm$^{-1}$):3345,3195,1770,1746,1681.

EXAMPLE 42

(3RS,5SR)-3-[N-(L-2-N-Benzyloxycarbonylamino-3-methylbutyryl)aminoacetyl]oxymethyl-4-oxa-1-azabicyclo[3.2.0]heptan-7-one (42A) and (3RS, 5SR)-3-[N-(L-2-Amino-3-methylbutyryl) aminoacetyl]oxymethyl-4-oxa-1-azabicyclo[3.2.0] heptan-7-one hydrochloride(42B)

According to the same manner described as in example 40, L-(2-N-benzyloxycarbonylamino-3-methylbutyl) aminoacetic acid was coupled with (3RS,5SR)-3-Bromomethyl-4-oxa-1-azabicyclo[3.2.0]heptan-7-one and N-protected title compound(42A) was obtained as off-white solid.

Yield:83%.

m.p.:143–145° C.

$^1$H NMR(CDCl$_3$,δ):0.94(3H,d,J=6.8),0.98(3H,d,J=6.8), 2.09–2.25(1H,m), 2.73–2.88(2H,m),3.29(1H,dd,J=16.3, 2.4),3.93–4.31(7H,m),4.48–4.59 (1H,m),5.11(2H,s), 5.32–5.40(2H,m),6.58(1H,br.t),7.34(5H,s).

IR(Nujol,cm$^{-1}$):3295,1793,1750,1687,1647,1619.

The benzyloxycarbonyl group was hydrogenolysed according to the same manner described as in example 40, the title compound(42B) was obtained as solid.

Yield:64%.

$^1$H NMR(DMSO-d$_6$,δ):0.91(6H,d,J=6.8),2.02–2.12(1H, m),2.66–2.76(2H,m), 3.29(1H,dd,J=16.1,2.6),3.62–4.17 (6H,m),4.40–4.55(1H,m),5.26(1H,d, J=2.5),8.25(3H,br.s), 9.0(1H,br.t).

IR(Nujol,cm$^{-1}$):3195,1776,1750,1677,1621.

EXAMPLE 43

(3RS,5RS)-3-N-(Aminoacetyl)aminomethyl-4-oxa-1-azabicyclo[3.2.0]heptan-7-one hydrochloride(43)

Azidoacetamide compound, obtained in reference example 9 (890 mg), was hydrogenated in presence of 5% Palladium on activated carbon(800 mg) in Ethanol(20 ml) at 50 psi for 2 hr. After removal of catalyst by filtration, 3.0 ml of 1N-HCl was added under cooling condition and solvent was removed in vacuo. The residue was purified on HP-20 column using water as eluent and the title compound was obtained after lyophilization as yellow solid(43).

Yield:62%.

$^1$H NMR(CDCl$_3$,δ):2.70(1H,dd,J=6.5,11.6),2.79(1H,d,J=16.4),3.19–3.44(3H,m),3.56(2H,s),3.82(1H,dd,J=6.5,11.6),4.27–4.39(1H,m),5.34 (1H,d,J=2.6),8.21(2H,br.s),8.72(1H,br.t,J=5.6).

IR(Nujol,cm$^{-1}$):3255,1768.

EXAMPLE 44

(3RS,5RS)-3-N-(N-Acetylaminoacetyl) aminomethyl-4-oxa-1-azabicyclo[3.2.0]heptan-7-one (44)

Acetic anhydride(17 ml) was added dropwise at 5° C. to a mixture of N-(aminoacetyl)aminomethyl amido derivative which was obtained in example 45(20 mg) and Triethylamine(17 mg) in Dichloromethane(1 ml). The mixture was stirred under same condition for 30 minutes. The reaction mixture was purified by silicagel column chromatography using Acetone as eluent and title compound(44) was obtained as white solid.

Yield:44%.

m.p.142–144° C.

$^1$H NMR(CDCl$_3$,δ):1.85(3H,s),2.66(1H,dd,J=6.4,11.5), 2.78(1H,d,J=16.3),3.14–3.38(3H,m),3.65(2H,d,J=10.2), 3.77(1H,dd,J=6.6,11.6), 4.24–4.36 (1H,m),5.30(1H,d,J=2.6),7.99–8.08(2H,m).

IR(Nujol,cm$^{-1}$):3280,3095,1800,1636.

EXAMPLE 45

(3RS,5RS)-3-[N-(L-2-N-Benzyloxycarbonylamino-3-methylbutyryl)aminoacetyl]aminomethyl-4-oxa-1-azabicyclo[3.2.0]heptan-7-one (45A) and (3RS, 5RS)-3-[N-(L-2-amino-3-methylbutyryl) aminoacetyl]aminomethyl-4-oxa-1-azabicyclo[3.2.0] heptan-7-one hydrochloride(45B)

According to the same manner as described in example 41, N-protected title compound(45A) was obtained as solid.

Yield:23%.

$^1$H NMR (DMSO-d$_6$,δ):0.79(6H,m),1.84–1.94(1H,m), 2.54–2.74(2H,m),3.15–3.29(5H,m),3.62–3.80(3H,m), 4.19–4.25(1H,m),4.96(2H,s),5.23(1H,d, J=2.6),7.29(5H,s), 7.82(1H,br.t),8.15(1H,br.s).

N-protected amide derivative, obtained as above, was deprotected as same manner described in example 43 and the title compound(45B) was obtained as solid.

Yield:0.40 g(70%).

$^1$H NMR(DMSO-d$_6$,δ):0.80(6H,m),1.94–2.10(1H,m), 2.60–2.74(2H,m),3.05– 3.35(5H,m),3.50–3.80(3H,m),5.25 (1H,d,J=2.6),8.35(3H,br.s),8.80 (1H,br.s).

IR(Nujol,cm$^{-1}$):3195,1782,1718,1678,1653,1603.

EXAMPLE 46

(3RS,5RS)-3-N-[N-(L-2-N-Benzyloxycarbonylamino-3-carboxypropanoyl) aminoacetyl]aminomethyl-4-oxa-1-azabicyclo[3.2.0] heptan-7-one (46A) and (3RS,5RS)-3-N-[N-(L-2-Amino-3-carboxypropanoyl)aminoacetyl] aminomethyl-4-oxa-1-azabicyclo[3.2.0]heptan-7-one (46B)

Azidoacetamide derivative of clavam compound, obtained in example 43, was coupled with protected aspartic acid derivative using similar method described in example 41 and the protected title compound was obtained(46A).

Yield:42%.

$^1$H NMR(CDCl$_3$,δ):2.62–2.88(2H,m),2.76(1H,d,J=16.6), 3.10–3.25(2H,m), 3.34–3.42(2H,m),3.77–4.17(3H,m), 4.30–4.40(1H,m),4.53–4.63(1H,m), 5.13(4H,s),5.28(1H,t, J=3.1),5.75–5.82(1H,m),6.67–6.75(1H,m),6.94–7.03(1H, m),7.30–7.38(10H,m).

0.5 g of the protected compound and 0.5 g of 5% Palladium on activated carbon in 10 ml Methanol was stirred under Hydrogen atmosphere at normal pressure for 2.5 hrs. Later the catalyst was filtered through celite and filtrate was concentrated. Acetonitrile was added to the residue and solid was collected by filtration(46B).

Yield:34%.

m.p.:200° C.(dec.).

$^1$H NMR(CDCl$_3$,δ):2.64–2.69(1H,m),2.77(1H,d,J=16.2), 3.08–3.85(6H,m), 3.32 (1H,d,J=13.4),4.25–4.38(1H,m), 5.30(1H,d,J=2.4),8.25–8.56 (2H,m).

IR(Nujol,cm$^{-1}$):3290,1773.

EXAMPLE 47

(3RS,5RS)-3-N-[N-(D-4-N-benzyloxycarbonylamino-4-benzyloxycarbonylbutyryl)aminoacetyl] aminomethyl-4-oxa-1-azabicyclo[3.2.0]heptan-7-one (47A) and (3RS,5RS)-3-N-[N-(D-4-Amino-4-carboxybutyryl)aminoacetyl]aminomethyl-4-oxa-1-azabicyclo[3.2.0]heptan-7-one(47A)

(3RS,5RS)-3-[N-(Azidoacetyl)aminomethyl]-4-oxa-1-azabicyclo[3.2.0]heptan-7-one, obtained in example 43, was coupled with [4-(Benzyloxycarbonylamino)-4-benzyloxycarbonyl]butyric acid using similar method described in example 41 and the protected title compound was obtained(47A).

Yield:21%.

m.p.:45° C.

$^1$H NMR(CDCl$_3$,δ):1.97–2.19(1H,m),2.17–2.30(1H,m), 2.40–2.50(2H,m), 2.73(1H,dd,J=6.1,11.6),3.25(1H,d,J= 16.2),3.94(1H,dd,J=6.9,11.6), 4.05–4.20(4H,m),4.40–4.55 (2H,m),5.10(2H,m),5.17(2H,m),5.30(1H,t, J=2.8),5.39 (br.s),7.35(10H,s).

IR(Neat,cm$^{-1}$):3355,1784,1739,1525.

This protected amide derivative obtained above was deprotected by using same method as described in example 46 and the title compound(47B) was obtained as solid.

Yield:10%.

m.p.:220° C.(dec).

$^1$H NMR(DMSO-d$_6$,δ):1.90–2.04(2H,m),2.75(1H,dd,J= 5.9,16.4),2.50–2.57 (4H,m),2.80(1H,d,J=16.4),3.33(1H,dd, J=2.6,16.2),3.84(1H,dd,J=7.1, 11.6),4.12(2H,d,J=3.4), 4.22–4.47(1H,m),5.29(1H,d,J=2.5),5.08–5.21 (1H,br.d).

EXAMPLE 48

(3RS,5SR)-3-(L-2-N-Benzyloxycarbonylaminopropanoyl)oxymethyl-4-oxa-1-azabicyclo[3.2.0]heptan-7-one(48A) and (3RS,5SR)-3-(L-2-Aminopropanoyl)oxymethyl- 4-oxa-1-azabicyclo[3.2.0]heptan-7-one hydrochloride (48B)

According to the same method described in example 40, N-protected title compound(48A) was obtained as oil.

Yield:68%.

$^1$H NMR(CDCl$_3$,δ):1.44(3H,d,J=7.2),2.70–2.87(1H,m), 2.84(1H,d,J=16.2),3.27(1H,d,J=16.0),3.98(1H,dd,J=7.1, 11.6),4.18–4.56(2H,m), 4.30–4.65(2H,m),5.12(2H,s), 5.18–5.30(1H,m),5.32(1H,s),7.35(5H,s).

IR(Neat,cm$^{-1}$):3550,1784,1748,1720,1525.

The N-protected ester derivative obtained above was deprotected by catalytic hydrogenation in Methanol using 5% Palladium on activated carbon at room temperature (50 psi, 1 hr). After removal of catalyst, 1N-HCl(1.7 ml) was added to the reaction mixture under cooling condition and resulted solution was then purified by HP-20 column chromatography using water as eluent. The title compound(48B) was obtained after lyophilization as solid.

Yield:15%.

1H NMR(DMSO-d$_6$,δ):1.43(3H,d,J=7.4),2.70–2.89(1H,m),2.80(1H,d,J=15.7),3.26–3.40(1H,m),3.88(1H,dd,J=6.7,11.8),4.02–4.37(4H,m), 4.50–4.70 (1H,m),5.35(1H,t,J=3.4),8.57(2H,br.s).

IR(Nujol,cm$^{-1}$):3400,3275,1746.

EXAMPLE 49

(3RS,5SR)-3-[L-2-N-(L-2-N-Benzyloxycarbonylamino-3-methylbutyryl) aminopropanoyl]oxymethyl-4-oxa-1-azabicyclo [3.2.0]heptan-7-one (49A) and (3RS,5SR)-3-[L-2-N-(L-2-Amino-3-methylbutyryl)amino propanoyl] oxymethyl-4-oxa-1-azabicyclo[3.2.0]heptan-7-one hydrochloride(49B)

According to the same method as described in example 41, protected title compound(49A) was obtained as an off-white solid.

Yield:65%.

m.p.:167–169° C.

$^1$H NMR (CDCl$_3$,δ):0.93(3H,d,J=6.8),0.98(3H,d,J=6.8), 1.35(3H,d,J=2.04–2.18(1H,m),2.73–2.89(2H,m),3.33(1H,dd,J=16.2,2.6),3.94–4.03 (2H,m),4.21–4.25(2H,m), 4.55–4.62(2H,m),5.11(2H,s),5.35(2H,br.s), 6.30(1H,d,J=7.1),7.35(5H,s).

IR (Nujol,cm$^{-1}$):3315,1785,1746,1688,1648.

The N-protected ester derivative was deprotected as same manner described in example 40 and the title compound (49B) was obtained as solid.

Yield:66%.

$^1$H NMR(DMSO-d$_6$,δ):0.98(6H,d,J=6.8),1.35(3H,d,J=7.2),2.12–2.15(1H, m),2.75–2.83(2H,m),3.31–3.38(1H,m),3.64–4.56(6H,m),5.35(1H,d,J=2.9),8.30(3H,br.s),9.06(1H,br.d,J=6.6).

IR(Nujol,cm$^{-1}$):3120,1792,1763,1740,1683,1650.

EXAMPLE 50

(3RS,5RS)-3-N-(L-2-N-Benzyloxycarbonylaminopropanoyl)aminomethyl-4-oxa-1-azabicyclo[3.2.0]heptan-7-one(50A) and (3RS,5RS)-3-N-(L-2-Aminopropanoyl) aminomethyl-4-oxa-1-azabicyclo[3.2.0]heptan-7-one hydrochloride(50B)

According to the same procedure described in example 43, N-protected title compound(50A) was obtained.

Yield:68%.

$^1$H NMR(CDCl$_3$,δ):1.42(3H,d,J=17.3),2.72–2.57(1H,m),2.81(1H,d,J=16.6),3.48(1H,dd,J=3.4,16.6),3.33–3.57(2H,m),3.85–4.00(1H,m), 4.16–5.76(2H,m),5.12(2H,s),5.26–5.31(1H,m),6.39(1H,br.s),7.33 (5H,s).

IR(Neat,cm$^{-1}$):3295,1782,1653,1533.

The title compound(50B) was obtained after deprotection as described in example 43, followed by salt formation.

1H NMR(DMSO-d$_6$,δ):1.35(3H,d,J=6.9),2.65–2.70(1H,m),2.79(1H,dd,J=3.1,16.4),3.10–3.50(3H,m),3.77–3.90(2H,m),4.27–5.92(1H,m),5.32 (1H,t,J=3.1),8.12 (2H,br.s),8.68 (1H,m).

IR(Nujol,cm$^{-1}$):3380,3230,1774,1670,1562.

EXAMPLE 51

(3RS,5SR)-3-(D-2-N-Benzyloxycarbonylaminopropanoyl)oxymethyl-4-oxa-1-azabicyclo[3.2.0]heptan-7-one(51A) and (3RS,5SR)-3-(D-2-Aminopropanoyl)oxymethyl-4-oxa-1-azabicyclo[3.2.0]heptan-7-one hydrochloride (51B)

According to the same procedure described in example 43, N-protected title compound(51A) was obtained as oil.

Yield:58%.

$^1$H NMR(CDCl$_3$,δ):1.44(3H,d,J=7.2),2.20–2.56(1H,m),5.68(1H,d,J=16.3),6.54(1H,d,J=15.9),3.97(1H,dd,J=7.0,11.6),4.17–4.25(2H,m), 4.38–4.63(2H,m),5.11(2H,s),5.25 (1H,br.d,J=6.4),5.32(1H,s),7.35 (5H,m).

IR(Neat,cm$^{-1}$):3355,1704,1748,1720,1526.

The title compound(51B) was obtained after deprotection as described in example 43, followed by salt formation.

Yield:18%.

$^1$H NMR(DMSO-d$_6$,δ):2.87(3H,d,J=7.4),2.71–2.92(2H,m),3.30–3.94 (1H,m),3.88(1H,dd,J=6.9,11.8),3.96–4.44 (3H,m),4.50–4.69(1H,m), 5.35(1H,t,J=3.5),8.57(1H,br.s).

IR(Nujol,cm$^{-1}$):3400,1746,1645.

EXAMPLE 52

(3RS,5SR)-3-{D-2-N-[D-2-N-(Thiophen-2-yl) acetylaminopropanoyl]aminopropanoyl}oxymethyl-4-oxa-1-azabicyclo[3.2.0]heptan-7-one (52)

According to the similar method as described in example 40, the title compound(52) was obtained as solid.

Yield:

m.p.:122–125° C.

$^1$H NMR(CDCl$_3$,δ):1.34(3H,d,J=7.0),1.40(3H,d,J=7.2), 2.80(1H,dd,J=6.3,17.9),2.85(1H,d,J=16.4),3.30(1H,dd,J=2.6,16.2),3.78(2H,s), 3.97 (1H,dd,J=6.7,11.6),4.20–4.26 (2H,m),4.47–4.55(2H,m),5.32–5.35 (1H,t,J=3.3),6.23 (1H,br.d,J=7.1),6.67(1H,br.d,J=7.1),6.95–7.01 (2H,m), 7.24–7.26(1H,m).

IR(CHCl$_3$,cm$^{-1}$):3295,1778,1747,1646.

EXAMPLE 53

(3RS,5RS)-3-N-(D-2-N-Benzyloxycarbonylaminopropanoyl)aminomethyl-4-oxa-1-azabicyclo[3.2.0]heptan-7-one(53A) and (3RS,5RS)-3-N-(D-2-Aminopropanoyl) aminomethyl-4-oxa-1-azabicyclo[3.2.0]heptan-7-one hydrochloride(53B)

According to the same method described in example 43, N-protected title compound(53A) was obtained as oil.

Yield:60%.

$^1$H NMR(CDCl$_3$,δ):1.42(3H,d,J=17.3),2.72–2.57(1H,m), 2.81(1H,d,J=16.6),3.48(1H,dd,J=3.3,16.6),3.33–3.57(2H,m),3.85–4.00(1H,m), 4.16–5.76(2H,m),5.12(2H,s),5.26–5.31(1H,m),6.39(1H,br.s),7.33 (5H,s).

IR(Neat,cm$^{-1}$):3295,1782,1653,1533.

The title compound(53B) was obtained after deprotection as described in example 43, followed by salt formation.

Yield:73%.

1H NMR(DMSO-d$_6$,δ):1.35(3H,d,J=6.9),2.65–2.70(1H,m),2.79(1H,dd,J=3.1,16.4),3.10–3.50(3H,m),3.77–3.90(2H,m),4.27–5.92(1H,m),5.32 (1H,t,J=3.1),8.12 (2H,br.s),8.68 (1H,br.s).

IR(Nujol,cm$^{-1}$):3380,3230,1774,1670,1562.

EXAMPLE 54

(3RS,5SR)-3-(L-2-N-Benzyloxycarbonylamino-3-methylbutyryl)oxymethyl-4-oxa-1-azabicyclo[3.2.0]heptan-7-one(54A) and (3RS,5SR)-3-(L-2-Amino-3-methylbutyryl)oxymethyl-4-oxa-1-azabicyclo[3.2.0]heptan-7-one hydrochloride(54B)

According to the same procedure described in example 43, N-protected title compound(54A) was obtained as oil.
Yield:49%.
$^1$H NMR(CDCl$_3$,δ):0.91(3H,d,J=6.9),0.98(3H,d,J=6.8), 2.13–2.22(1H, m),2.84(2H,d,J=16.3),3.23–3.33(1H,m),4.00 (1H,dd,J=7.0,11.6),4.17–4.33(3H,m),4.50–4.60(1H,m),5.11 (2H,s),5.20–5.26(1H,m),5.33(1H,s), 7.36(5H,s).

The title compound(54B) was obtained after deprotection as described in example 43, followed by salt formation.
Yield:71%.
$^1$H NMR(DMSO-d$_6$,δ):0.95–0.99(6H,m),2.16–2.22(1H, m),2.76–2.86 (2H,m),3.32–3.40(1H,m),3.84–4.32(4H,m), 4.57–4.60(1H,m),5.35(1H,d, 2.6),8.54(3H,br.s).

IR(Nujol,cm$^{-1}$):1778,1742,1683,1646.

EXAMPLE 55

(3RS,5SR)-3-[L-2-(N-Benzyloxycarbonylaminoacetyl)amino-3-methylbutyryl]oxymethyl-4-oxa-1-azabicyclo[3.2.0]heptan-7-one (55A) and (3RS,5SR)-3-[L-2-(N-Aminoacetyl)amino-3-methylbutyryl]oxymethyl-4-oxa-1-azabicyclo[3.2.0]heptan-7-one hydrochloride (55B)

According to the similar method described as in example 40, N-protected title compound(55A) was obtained as oil.
Yield:81%.
$^1$H NMR(CDCl$_3$,δ):0.93(3H,d,J=6.8),0.95(3H,d,J=6.8), 2.05–2.28(1H,m), 2.74–2.90(2H,m),3.30(1H,dd,J=16.1, 2.4),3.83–4.05(3H,m),4.12–4.35 ($^2$H,m),4.48–4.66(2H,m), 5.11(2H,s),5.34–5.47(2H,br.s),6.50(1H,d, J=8.0),7.35(5H, s).

IR(Nujol,cm$^{-1}$):3345,1784,1740,1680.

The title compound(55B) was obtained after deprotection as described in example 40, followed by salt formation.
Yield:48%.
$^1$H NMR(DMSO-d$_6$,δ):0.93(6H,d,J=6.6),2.04–2.14(1H, m),2.76–2.83(2H,m), 3.32–3.40(1H,m),3.63–4.31(6H,m), 4.54–4.59(1H,m),5.33(1H,dd,J=7.0, 2.5),8.82(3H,br.s),8.86 (1H br,s).

IR(Nujol,cm$^{-1}$):3185,1779,1735,1681.

EXAMPLE 56

(3RS,5SR)-3-[L-2-N-(L-2-N-Benzyloxycarbonylamino-3-methylbutyryl)amino-3-methylbutyryl]oxymethyl-4-oxa-1-azabicyclo[3.2.0]heptan-7-one(56A) and (3RS,5SR)-3-[L-2-N-(L-2-Amino-3-methylbutyryl)amino-3-methylbutyryl]oxymethyl-4-oxa-1-azabicyclo-[3.2.0]heptan-7-one hydrochloride(56B)

According to the similar method described in example 41, protected title compound(56A) was obtained.
Yield:77%.
$^1$H NMR(CDCl$_3$,δ):0.89–0.98(12H,m),2.06–2.21(2H,m), 2.73–2.88(2H,m), 3.29(1H,d,J=16.2),3.93–4.25(4H,m), 4.52–4.59(2H,m),5.11(2H,s),5.33 (1H,d,J=2.8),5.45(1H,d, J=8.8),6.54(1H,d,J=8.4),7.34(5H,s).

The title compound(56B) was obtained after deprotection as described in example 40, followed by salt formation.
Yield:64%.
$^1$H NMR(DMSO-d$_6$,δ):0.94–1.00(12H,d,J=6.7),2.10–2.20 (2H,m),2.71–2.84 (2H,m),3.32–3.40(2H,m),3.80–3.90(2H, m),4.15–4.23(3H,m),4.50–4.10 (1H,m),5.34(1H,d,J=2.8), 8.33(3H,br.s),8.75(1H,d,J=7.1).

IR(Nujol,cm$^{-1}$):3325,3200,1793,1762,1741,1685,1653.

EXAMPLE 57

(3RS,5RS)-3-N-[L-2-N-(L-2-N-Benzyloxycarbonylamino-3-benzyloxycarbonylpropanoyl)amino-3-methylbutyryl]oxymethyl-4-oxa-1-azabicyclo[3.2.0]heptan-7-one(57A) and (3RS,5RS)-3-N-[L-2-N-(L-2-Amino-3-carboxypropanoyl)amino-3-methylbutyryl]oxymethyl-4-oxa-1-azabicyclo[3.2.0]heptan-7-one(57B)

According to the similar method as described in example 46, protected title compound(57A) was obtained.
Yield:89%.
$^1$H NMR(CDCl$_3$,δ):0.90(6H,t,J=7.2),2.12–2.18(1H,m), 2.69–2.88 (3H,m),3.08(1H,dd,J=4.2,17.4),3.29(1H,d,J= 16.4),3.92–4.07(1H, m),4.10–4.25(2H,m),4.43–4.62(3H, m),5.13(4H,s),5.30–5.34(1H,m), 5.97–6.04(1H,br.d), 6.95–7.04(1H,br.d),7.35(10H,d,J=3.0).

IR(Nujol,cm$^{-1}$):3425,1783,1737,1679.

According to the similar method described as in example 46,the title compound(57B) was obtained as solid.
Yield:72%.
m.p.190° C.(dec.).
1H NMR(DMSO-d$_6$,δ):0.90(6H,d,J=6.3),2.0–2.40(2H, m),2.68–2.85(2H,m), 3.16(1H,s),3.25–3.39(1H,m), 3.63–3.90(2H,m),4.08–4.26(3H,m),4.48–4.58(1H,m),5.32 (1H,s),8.63–8.75(1H,m).

IR(Nujol,cm$^{-1}$):1783,1742.

EXAMPLE 58

(3RS,5RS)-3-N-(L-2-N-Benzyloxycarbonylamino-3-methylbutyryl)aminomethyl-4-oxa-1-azabicyclo[3.2.0]heptan-7-one (58A) and (3RS,5RS)-3-N-(L-2-Amino-3-methylbutyryl)aminomethyl-4-oxa-1-azabicyclo[3.2.0]heptan-7-one hydrochloride(58B)

According to the same procedure described in example 43, N-protected title compound(58A) was obtained as solid.
Yield:44%.
$^1$H NMR(CDCl$_3$,δ):0.97(6H,d,J=7.0),2.15(1H,q,J=6.8), 2.58–2.70 (1H,m),2.82(1H,d,J=16.6),3.28(1H,d,J=16.3), 3.34–3.62(2H,m),3.36–4.01(2H,m),4.25–4.41(1H,m),5.12 (2H,d,J=1.4),5.28(1H,d,J=2.5),5.25 (1H,br.s),6.19(1H,br.s), 7.36(5H,s).

IR(Nujol,cm$^{-1}$):3295,1781,1684,1646,1532.

The title compound(58B) was obtained after deprotection as described in example 43, followed by salt formation.
Yield:57%.
$^1$H NMR(DMSO-d$_6$,δ):0.93(6H,d,J=6.8),2.00–2.16(1H, m),2.64–2.69(1H, m),2.79(1H,dd,J=3.7,16.6),3.29–3.50 (4H,m),3.60(1H,d,J=4.8),3.77–3.88(1H,m),4.27–4.42(1H, m),5.34(1H,s),8.18(2H,br.s),8.68–8.81 (1H,m).

IR(Nujol,cm–1):3350,3225,1716,1670.

EXAMPLE 59

(3RS,5RS)-3-N-(D-2-N-Benzyloxycarbonylamino-3-methylbutyryl)aminomethyl-4-oxa-1-azabicyclo[3.2.0]heptan-7-one (59A) and (3RS,5RS)-3-N-(D-2-Amino-3-methylbutyryl)aminomethyl-4-oxa-1-azabicyclo[3.2.0]heptan-7-one hydrochloride(59B)

According to the same procedure described in example 43, N-protected title compound(59A) was obtained as solid.

Yield:55%.

m.p.:141–143° C.

$^1$H NMR(CDCl$_3$,δ):0.91–0.99(6H,m),2.15(1H,q,J=6.4), 2.59–2.72(1H,m), 2.82(1H,d,J=16.3),3.28(1H,d,J=16.3), 3.36–3.62(2H,m),3.39–4.00 (2H,m),4.28–4.41(1H,m),5.12 (2H,s),5.25(1H,d,J=2.6),5.31(1H,br.s), 6.20(1H,br.s),7.36 (5H,s).

The title compound(59B) was obtained after deprotection as described in example 43, followed by salt formation.

Yield:31%.

$^1$H NMR(DMSO-d$_6$,δ):0.93(6H,d,J=6.8),2.00–2.16(1H, m),2.64–2.69(1H, m),2.79(1H,dd,J=3.7,16.6),3.29–3.50 (4H,m),3.60(1H,d,J=4.8),3.77–3.88(1H,m),4.27–4.42(1H, m),5.34(1H,s),8.18(2H,br.s),8.68–8.81 (1H,m).

IR(Nujol,cm−1):3350,3225,1716,1670.

EXAMPLE 60

(3RS,5SR)-3-(D-2-Benzyloxycarbonylamino-3-methylbutyryl)oxymethyl-4-oxa-1-azabicyclo[3.2.0] heptan-7-one(60A) and (3RS,5SR)-3-(D-2-Amino-3-methylbutyryl)oxymethyl-4-oxa-1-azabicyclo [3.2.0]heptan-7-one hydrochloride(60B)

According to the same procedure described in example 43, N-protected title compound(60A) was obtained.

Yield:85%.

$^1$H NMR(CDCl$_3$,δ):0.91(3H,d,J=6.9),0.99(3H,d,J=6.9), 2.10–2.22(1H, m),2.79–2.89(2H,m),3.27(1H,d,J=16.1), 3.93–4.33(3H,m),4.51–4.56 (1H,m),5.11(2H,s),5.24(1H,d, J=9.0),5.32(1H,d,J=2.6),7.35(5H,s).

The title compound(60B) was obtained after deprotection as described in example 43, followed by salt formation.

Yield:70%.

$^1$H NMR(DMSO-d$_6$,δ):0.88–0.96(6H,m),2.09–2.15(1H, m),2.68–2.96(2H, m),3.27–3.40(1H,m),3.77–4.24(4H,m), 4.30–4.53(1H,m),5.28(1H,d, J=2.6),8.46(3H,br.s).

IR(Nujol,cm−1):3255,1781,1748,1685.

EXAMPLE 61

(3RS,5SR)-3-(D-2-Acetylamino-3-methylbutyryl) oxymethyl-4-oxa-1-azabicyclo[3.2.0]heptan-7-one (61)

According to the same procedure described in example 44, title compound(61) was obtained.

Yield:49%.

$^1$H NMR(DMSO-d$_6$,δ):0.90(6H,m),2.05(3H,s),3.10–3.15 (1H,m),2.75–2.90 (2H,m),3.30(1H,d,J=16.2),3.90–4.15(6H, m),5.35(1H,d,J=2.6),5.92 (1H,d,J=2.5).

IR(Nujol,cm−1):3315,2945,1794,1743,1665.

EXAMPLE 62

(3RS,5SR)-3-[D-2-N-(D-2-N-Benzyloxycarbonylamino-3-methylbutyryl)amino-3-methylbutyryl]oxymethyl-4-oxa-1-azabicyclo[3.2.0] heptan-7-one(62A) and (3RS,5SR)-3-[D-2-N-(D-2-Amino-3-methylbutyryl)amino-3-methylbutyryl] oxymethyl-4-oxa-1-azabicyclo[3.2.0]heptan-7-one hydrochloride(62B)

According to the same procedure described in example 41, N-protected title compound(62A) was obtained.

Yield:70%.

$^1$H NMR(CDCl$_3$,δ):0.92–0.99(12H,m),2.09–2.22(2H,m), 2.74–2.89(2H,m), 3.30(1H,J=16.2),3.94–4.24(4H,m), 4.52–4.59(2H,m),5.12(2H,s),5.33 (2H,m),6.36(1H,d,J=8.5), 7.34(5H,s).

The title compound(62B) was obtained after deprotection as described in example 43, followed by salt formation.

Yield: 58%.

$^1$H NMR(DMSO-d$_6$,δ):0.96(12H,d,J=6.7),2.06–2.16(2H, m),2.71–2.82 (2H,m),3.38–3.39(2H,m),3.78–3.89(2H,m), 4.17–4.23(3H,m),4.51–4.55 (1H,m),5.34(1H,d,J=2.8),8.33 (3H,br.s),8.73(1H,d,J=7.1).

IR(Nujol,cm−1):3355,3215,1784,1748,1681,1654.

EXAMPLE 63

(3RS,5RS)-3-N-(L-2-N-Benzyloxycarbonylamino-3-phenylpropanoyl)aminomethyl-4-oxa-1-azabicyclo [3.2.0]heptan-7-one(63A) and (3RS,5RS)-3-N-(L-2-Amino-3-phenylpropanoyl)aminomethyl-4-oxa-1-azabicyclo[3.2.0]heptan-7-one hydrochloride(63B)

According to the same procedure described in example 43, N-protected title compound(63A) was obtained as white solid.

Yield:55%.

m.p.:149–151° C.

$^1$H NMR(CDCl$_3$,δ):2.44(1H,dd,J=7.3,11.7),2.56(1H,dd, J=7.2,11.9), 2.76(1H,d,J=16.7),2.96–3.37(4H,m),3.77–3.90 (1H,m),4.10–4.30(1H, m),4.31–4.43(1H,m),5.04(1H,d,J= 2.6),5.09(2H,s),5.18(1H,d,J=2.6), 5.28(1H,br.s),5.98(1H, br.s),7.27–7.35(5H,m).

IR(Nujol,cm−1):3315,1783,1681,1665.

The title compound(63B) was obtained after deprotection as described in example 43, followed by salt formation.

m.p.:220–233° C.(dec.).

$^1$H NMR(DMSO-d$_6$,δ):2.45(1H,dd,J=6.7,11.8),2.62(1H, dd,J=6.7,11.6), 2.76(1H,d,J=16.3),3.06–3.39(10H,m), 3.59–3.78(2H,m),4.04(1H,br.t, J=6.7),4.17–4.18 (1H,m), 5.22(1H,d,J=2.3),5.28(1H,d,J=2.4),7.22–7.36(10H,m),8.37 (4H,br.s),8.74(2H,m).

IR(Nujol,cm−1):3205,1776,1561.

EXAMPLE 64

(3RS,5RS)-3-N-[L-2-N-(L-2-N-Benzyloxycarbonylamino-3-carboxy propanoyl) amino-3-phenylpropanoyl]aminomethyl-4-oxa-1-azabicyclo[3.2.0]heptan-7-one(64A) and (3RS, 5RS)-3-N-[L-2-N-(L-2-Amino-3-carboxypropanoyl) amino-3-phenylpropanoyl]aminomethyl-4-oxa-1-azabicyclo[3.2.0]heptan-7-one(64B)

A mixture of compound63B, obtained in example 63 (500 mg), 3-N-Benzyloxycarbonylamino-3-benzyloxycarbonylpropanoic acid(822 mg), 1,3-Dicyclohexyl-carbidiimide (475 mg), Triethylamine(0.35 ml) in Dichloromethane(20 ml) was stirred at room temperature for 2 hrs. Resulted mixture was loaded on silicagel column, eluted with Hexane-Ethyl acetate(1:2–1:3) and protected dipeptide(64A) was obtained as solid.

Yield:51%.

$^1$H NMR(CDCl$_3$,δ):2.44–2.61(1H,m),2.76(1H,d,J=16.4), 2.90–3.12(3H, m),3.20(1H,dd,J=2.7,16.3),3.33(2H,t,J=5.3), 3.77–3.88(1H,m),4.19–4.23(1H,m), 4.52–4.61(1H,m),5.08 (2H,s),5.10(2H,s),5.20(1H,d,J=2.6),5.71(1H,br.s),6.27(1H, br.s),6.79(1H,br.d,J=7.7),7.16–7.36 (10H,m).

IR(Nujol,cm−1):3285,1782,1730,1693.

The protected compound, obtained above, was deprotected as in example 46 and the title compound(64B) was obtained as solid.

$^1$H NMR(DMSO-d$_6$,δ):1.70–1.96(1H,m),2.19–2.36(1H, m),2.67(1H,dd,J=6.4,11.5),2.78(1H,d,J=17.1),3.04–3.45

(3H,m),3.12(1H,dd,J=2.9, 16.5),3.78(1H,dd,J=6.5,11.5), 4.23–4.47(1H,m),5.31(1H,d,J=2.6), 6.72(2H,br.s),8.35(1H, br.s).

IR(Nujol,cm$^{-1}$):3300,1782.

EXAMPLE 65

(3RS,5SR)-3-(L-3-N-Benzyloxycarbonylamino-3-benzyloxycarbonyl propanoyl)oxymethyl-4-oxa-1-azabicyclo[3.2.0]heptan-7-one(65A) and (3RS, 5SR)-3-(L-3-Amino-3-carboxypropanoyl) oxymethyl-4-oxa-1-azabicyclo[3.2.0]heptan-7-one (65B)

A mixture of (3RS,5SR)-3-Bromomethyl-4-oxa-1-azabicyclo[3.2.0]heptan-7-one(1.0 g), (3-N-Benzyloxycarbonylamino-3-benzyloxycarbonyl)propanoic acid(2.5 g), Cesium carbonate (1.63 g) and Hexamethylphosphoric triamide(10 ml) was heated with stirring at 60–70° C. for 16 hrs. The reaction mixture was then diluted with Ethyl acetate, washed with water, brine and dried over Magnesium sulfate. The residual oil after removal of solvent in vacuo, was purified by silicagel column chromatography eluted with Hexane-Ethyl acetate (1:1). The desired title compound(65A) was obtained as oil.

Yield:86%.

$^1$H NMR(CDCl$_3$,δ):2.62–3.26(5H,m),3.83–4.20(3H,m), 4.36–4.46(1H,m), 4.66–4.75(1H,m),5.10(2H,s),5.16(2H,s), 5.23–5.26(1H,m),5.74–5.84 (1H,m),7.30(10H,s).

IR(Nujol,cm$^{-1}$):3355,2965,1787,1745.

The protected ester, obtained above, was deprotected as described in example 46 and the title compound(65B) was obtained as solid.

Yield:69%.

m.p.:175° C.

$^1$H NMR(DMSO-d$_6$,δ):2.57–3.00(4H,m),3.23–3.70(2H, m),3.83–3.98(1H,m), 4.13–4.25(2H,m),4.53–6.67(1H,m), 5.39(1H,d,J=2.5).

IR(Nujol,cm$^{-1}$):3130,1793,1736.

EXAMPLE 66

(3RS,5SR)-3-(L-2-N-Benzyloxycarbonylamino-3-benzyloxycarbonyl propanoyl)oxymethyl-4-oxa-1-azabicyclo[3.2.0]heptan-7-one(66A) and (3RS, 5SR)-3-(L-2-Amino-3-carboxypropanoyl) oxymethyl-4-oxa-1-azabicyclo[3.2.0]heptan-7-one (66B)

According to the same procedure described in example 65, protected title compound(66A) was obtained.

Yield:74%.

$^1$H NMR(CDCl$_3$,δ):2.68–2.88(1H,m),2.79(1H,dd,J=3.4, 16.5),2.90–3.10 (1H,m),3.19(1H,d,J=16.3),3.84–3.96(1H, m),4.17–4.22(2H,m),4.41–4.56(1H,m),4.62–4.77(1H,m), 5.12(4H,s),5.26(1H,d,J=2.6),5.74(1H, br.d),7.34(5H,s),7.36 (5H,s).

IR(Neat,cm$^{-1}$):3355,1781,1753,1731,1518.

The protected compound, obtained above, was deprotected as described in example 46 and the title compound (66B) was obtained as solid.

Yield:55%.

m.p.:150–180° C.(dec.).

$^1$H NMR(DMSO-d$_6$,δ):2.77–2.84(1H,m),2.91(1H,dd,J= 4.3,11.2),2.94(1H, d,J=16.7),3.40(1H,dd,J=1.6,19.6),4.05 (1H,dd,J=7.0,11.9),4.28–4.52 (3H,m),4.70–4.79(1H,m), 5.46(1H,d,J=2.4).

IR(Nujol,cm$^{-1}$):3375,1776,1752.

EXAMPLE 67

(3RS,5RS)-3-N-(L-2-N-Benzyloxycarbonylamino-3-benzyloxycarbonyl propanoyl)aminomethyl-4-oxa-1-azabicyclo[3.2.0]heptan-7-one(67A) and (3RS, 5RS)-3-N-(L-2-Amino-3-carboxypropanoyl) aminomethyl-4-oxa-1-azabicyclo[3.2.0]heptan-7-one (67B)

(3RS,5RS)-3-Azidomethyl-4-oxa-1-azabicyclo[3.2.0] heptan-7-one, (1.0 g), was hydrogenated by using 10% Palladium on activated carbon(250 mg) at 50 psi for 1 hr. After removal of catalyst, L-(2-N-Benzyloxycarbonylamino-3-benzyloxycarbonyl)propanoic acid (2.55 g), and Triethylamine (0.1 ml) was added to the filtrate, followed by dropwise addition of a solution of 1,3-Dicyclohexylcarbodiimide (1.47 g) in Ethyl acetate(10 ml) under ice-cooled condition. After 1 hr stirring, the reaction mixture was loaded on silicagel column and eluted with Hexane-Ethyl acetate(2:3). The desired protected amide derivative(67A) was obtained as oil.

Yield: 50%.

$^1$H NMR(CDCl$_3$,δ):2.56–2.71(1H,m),2.81(1H,d,J=16.7), 3.06–3.18 (1H,m),3.26(1H,dd,J=2.8,16.4),3.36–3.52(2H, m),3.83–3.94(1H,m), 4.23–4.37(1H,m),4.50–4.64(1H,m), 5.13(4H,d,J=2.8),5.24–5.29(1H,m), 5.90(1H,br,d),6.71(1H, br,s),7.34(5H,s),7.36(5H,s).

IR(Neat,cm$^{-1}$):3330,1778,1727,1667,1529.

The protected amido derivative obtained above was deprotected as described in example 46 and the title compound(67B) was obtained as solid.

Yield:74%.

m.p.275–285° C.(dec.).

$^1$H NMR(DMSO-d$_6$,δ):2.65–2.86(3H,m),2.93(1H,d,J= 17.2),4.40(1H,dd, J=2.2,16.7),3.47–3.55(2H,m),4.00(1H, dd,J=6.6,11.9),4.23(1H,dd, J=5.6,7.4),4.51–4.56(1H,m), 5.43(1H,d,J=2.6).

IR(Nujol,cm$^{-1}$):3215,1677,1562.

EXAMPLE 68

(3RS,5SR)-3-(D-4-N-Benzyloxycarbonylamino-4-benzyloxycarbonyl butyryl)oxymethyl-4-oxa-1-azabicyclo[3.2.0]heptan-7-one(68A) and (3RS, 5SR)-3-(D-4-Amino-4-carboxybutyryl)oxymethyl-4-oxa-1-azabicyclo[3.2.0]heptan-7-one(68B)

According to the same procedure as example 65, protected title compound(68A) was obtained as oil.

Yield:48%.

$^1$H NMR(CDCl$_3$,δ):1.97–2.19(1H,m),2.17–2.30(1H,m), 2.40–2.50(2H,m), 2.73(1H,dd,J=6.1,11.6),3.25(1H,d,J= 16.2),3.94(1H,dd,J=6.9,11.6), 4.05–4.20(2H,m),4.40–4.55 (2H,m),5.10(2H,m),5.17(2H,m),5.30(1H,t, J=2.8),5.39 (br.s),7.35(10H,s).

IR(Neat,cm$^{-1}$):3355,1784,1739,1525.

The protected ester derivative obtained above was deprotected as described in example 46 and the title compound (68B) was obtained as solid.

Yield:82%.

m.p.:>250° C.(dec.).

$^1$H NMR(DMSO-d$_6$,δ):1.90–2.04(2H,m),2.75(1H,dd,J= 5.9,16.4),2.50–2.57 (2H,m),2.80(1H,d,J=16.4),3.33(1H,dd, J=2.6,16.2),3.84(1H,dd,J=7.1, 11.6),4.12(2H,d,J=3.4), 4.52–4.60(1H,m),5.32(1H,d,J=2.5).

EXAMPLE 69

(3RS,5RS)-3-N-(D-4-N-Benzyloxycarbonylamino-4-benzyloxycarbonyl butyryl)aminomethyl-4-oxa-1-azabicyclo[3.2.0]heptan-7-one(69A) and (3RS, 5RS)-3-N-(D-4-Amino-4-carboxybutyryl) aminomethyl-4-oxa-1-azabicyclo[3.2.0]heptan-7-one (69B)

According to the same procedure as example 67, protected title compound(69A) was obtained as solid.

Yield:22%.

¹H NMR(CDCl₃,δ):1.90–2.10(1H,m),2.11–2.35(3H,m), 2.60–2.72(1H,m), 2.81(1H,d,J=16.2),3.20–3.60(3H,m),3.92 (1H,dd,J=7.4,12.0),4.30–4.50(1H,m),5.11(2H,s),5.17(2H, s),5.30(1H,s),5.59(1H,br.s),6.16 (1H,br.s),7.35(10H,s).

IR(Neat,cm⁻¹):3345,1783,1720,1654,1533.

The protected amido derivative obtained above was deprotected as described in example 46 and the title compound(69B) was obtained as solid.

Yield:48%.

¹H NMR(DMSO-d₆,δ):1.74–1.83(1H,m),1.84–1.93(1H, m),2.26(2H,t,J=7.9),2.67(1H,dd,J=6.4,11.5),2.77(1H,d,J= 16.3),3.13–3.18(1H,m), 3.19–3.22(1H,m),3.25–3.33(1H, m),3.32(1H,dd,J=2.7,16.3),3.77(1H, dd,J=6.6, 11.6), 4.28–4.34(1H,m),5.31(1H,d,J=2.9),7,30(1H,br.s), 8.33 (1H.br,s).

EXAMPLE 70

(3RS,5SR)-3-(L-2-N-Benzyloxycarbonylamino-3-hydroxypropanyl)oxymethyl-4-oxa-1-azabicyclo [3.2.0]heptan-7-one (70)

780 mg (3.8 mmol) of (3RS,5SR)-3-Bromomethyl-4-oxa-1-azabicyclo[3.2.0]heptan-7-one and 1.0 g of sodium salt of L-(2-N-Benzyloxycarbonylamino-3-hydroxy)propanoic acid in 0.8 ml of Hexamethylphosphoric triamide was heated at 65° C. for 3 hrs. General work-up and purification gave the title compound as oil.

Yield:64%.

¹H NMR(CDCl₃,δ):2.19–2.32(1H,m),2.75–2.87(2H,m), 3.21–3.32(1H,dd, J=2.6,13.6),3.92–4.55(7H, m),5.13 (2H, s),5.32(H,s),5.66–5.74 (1H, m) 7.34 (5H, s).

IR(Nujol,cm⁻¹):3430,2963,1780,1751.

EXAMPLE 71

(3RS,5SR)-3-[L-2-N-(D-2-N-Benzyloxycarbonylaminopropanoyl)amino-3-hydroxypropanoyl]oxymethyl-4-oxa-1-azabicyclo [3.2.0]heptan-7-one(71)

600 mg (1.65 mmol) of compound(70) and 450 mg of 10% Palladium on activated carbon in 20 ml Ethyl acetate was shaken under Hydrogen atmosphere for 1 hr and filtered through celite. To the filtrate 370 mg (1.6 mmol) of D-2-(N-Benzyloxy-carbonyl)amino propanoic acid and 170 mg (0.80 mmol) of 1,3-Dicyclohexylcarbodiimide were added under cooling and stirred at room temperature for 3 hrs. The solid was removed by filtration and the solution was concentrated. The residue was purified by flash column using Ethyl acetate-Hexane(4:1) as eluent. The title compound(71) was obtained as solid.

Yield:3%.

m.p.: 150–155° C.

¹H NMR(CDCl₃,δ):1.41(3H,d,J=7.0),2.38(1H,s), 2.77–2.90(2H,m),3.27 (1H,dd,J=2.3,11.5),3.85–4.57(8H, m),5.12(2H,s),5.34(1H,s),5.95 (1H,d,J=7.2),7.35(5H,s),7.56 (1H,J=7.6).

EXAMPLE 72

(3RS,5SR)-3-L-(2-N-Benzyloxycarbonylamino-3-benzyloxypropanoyl)oxymethyl-4-oxa-1-azabicyclo [3.2.0]heptan-7-one(72)

According to the same procedure as example 61, the title compound (72) was obtained as oil.

Yield:94%.

¹H NMR(CDCl₃,δ):2.70–2.82(2H,m),3.14–3.22(1H,m), 3.66–3.74(1H,m), 3.84–3.95(2H,m),4.16–4.33(2H,m), 4.44–4.58(4H,m),5.12(2H,s),5.24 (1H,dd,J=2.3,6.7),5.62 (1H,d,J=4.5),7.25–7.36(10H,m).

IR(Neat,cm⁻¹):3345,1781,1718.

EXAMPLE 73

(3RS,5R)-3-[L-2-N-(D-2-N-Benzyloxycarbonylaminopropanoyl)amino-3-benzyloxypropanoyl]oxymethyl-4-oxa-1-azabicyclo [3.2.0]heptan-7-one(73)

According to the same procedure as example 41, the title compound (73) was obtained as solid.

Yield:34%.

m.p.:107–108° C.

¹H NMR(CDCl₃,δ):1.48(3H,d,J=2.8),2.68–2.80(2H,m), 3.14–3.22(1H,m), 3.60–3.70(1H,m),3.85–3.94(2H,m), 4.04–4.55(6H,m),4.70–4.78(1H,m), 5.10(2H,s),5.25(1H,dd, J=2.3,6.8),5.30–5.38(1H,m),6.85–6.92 (1H,m),7.25–7.34 (10H,m).

IR(Nujol,cm⁻¹):3315,1780.

EXAMPLE 74

(3RS,5SR)-3-[L-2-N-(L-2-N-Benzyloxycarbonylamino-3-methylbutyryl)amino-3-benzyloxypropanoyloxymethyl]-4-oxa-1-azabicyclo [3.2.0]heptan-7-one (74A) and (3RS,5SR)-3-[L-2-N-(L-2-N-Amino-3-methylbutyryl)amino-3-benzyloxypropanoyloxymethyl]-4-oxa-1-azabicyclo [3.2.0]heptan-7-one hydrochloride(74B)

According to the same procedure as example 41, protected title compound(74A) was obtained as solid.

Yield:51%.

m.p.:100–102° C.

¹H NMR(CDCl₃,δ):0.90–0.95(3H,d,J=3.0),0.95–1.04 (3H,d,J=2.8),2.10–2.18(1H,m),2.67–2.82 (2H,m),3.17–3.27 (1H,m),3.62–3.68(1H,m),3.86–3.96(2H,m),4.05–4.26(3H, m),4.42–4.56(3H,m),4.72–4.78 (1H,m),5.13 (2H,s),5.23.(H, dd,J=2.4,16.2),5.34(1H,d,J=4.5),6.58(1H,d,J=4.4), 7.25–7.36(10H,m).

IR(Nujol,cm⁻¹):3320,2970,1781.

The title compound(74B) was obtained after deprotection as described in example 43, followed by salt formation.

Yield:77%.

m.p.:168° C. (dec).

¹H NMR(DMSO-d₆,δ):0.98–1.18 (6H,m), 2.12–2.22(1H, m) 2.72–2.86(2H,m), 3.28–3.34(1H,m),3.68–3.94(4H,m), 4.20–4.28(2H,m),4.52–4.77(4H,m), 5.34(H, dd,J=2.5,16.2), 7.40(5H,s),8.24–8.32 (3H,s),9.06 (1H,d, J=8.1).

IR(Nujol,cm⁻¹):3335,1772,1678.

EXAMPLE 75

(3RS,5SR)-3-(L-2-Acetamido-3-hydroxypropanoyl) oxymethyl-4-oxa-1-azabicyclo[3.20]heptan-7-one (75A) and (3RS,5SR)-3-(2-Acetamido-3-acetoxypropanoyl)oxymethyl-4-oxa-1-azabicyclo [3.2.0]heptan-7-one(75B)

500 mg (1.3 mmol) of the compound 72 was deprotected as usual manner. To this 140 mg (1.37 mmol) of Triethylamine was added and cooled to 0° C. 110 mg (1.37 mmol) Acetyl chloride was added, stirred at the same temperature for 1 hr followed by at room temperature for 1 hr. The solution was filtered and the filtrate was concentrated. The compound was purified over silica gel using Ethyl acetate first and then Ethyl acetate-Acetone (5:1). Two fractions were collected. N-Acetyl compound(75A) and N,O-diacetyl compound(75B) were obtained.

Monoacetyl compound(75A):

Yield:39%.

$^1$H NMR(CDCl$_3$,δ):2.07(6H,s),2.75–2.90(2H,m), 3.25–3.38(1H,m),3.95–4.07(1H,m),4.24–4.36(3H,m), 4.50–4.60(2H,m),4.84–4.92(1H,m),5.34 (1H,d,J=2.5), 6.20–6.30(1H,m).

IR(Nujol,cm$^{-1}$):3335,2960,1779,1664.

Diacetyl compound(75B):

Yield:26%.

hu 1H NMR(CDCl$_3$,δ):2.08(3H,s),2.44(1H,t,J=6.9), 2.77–2.90(2H,m),3.30(1H,dd,J=2.8,12.2),3.95–4.40(5H,m), 4.54–4.64(1H,m),4.70–4.78 (1H,m),5.36(1H,d,J=2.6), 6.38–6.46(1H,m).

IR(Neat,cm$^{-1}$):3360,2968,1774,1653.

EXAMPLE 76

(3RS,5RS)-3-[N-(L-2-N-Benzyloxycarbonylamino-3-hydroxypropanoyl)aminomethyl]-4-oxa-1-azabicyclo[3.2.0]heptan-7-one (76A) and (3RS, 5RS)-3-[N-(L-2-Amino-3-hydroxypropanoyl) aminomethyl]-4-oxa-1-azabicyclo[3.2.0]heptan-7-one hydrochloride(76B)

According to the same procedure described in example 43, N-protected title compound(76A) was obtained as white solid.

Yield:38%.

m.p.:114–116,124.5–137° C.

$^1$H NMR(CDCl$_3$,δ):2.69(1H,dd,J=6.3,11.0,),2.81(1H,d, J=15.8),3.25 (1H,d,J=16.3),3.47(2H,t,J=5.3),3.62–3.77(1H, m),3.85–3.47(3H,m), 4.17–4.30(1H,m),4.30–4.43(1H,m), 5.13(2H,s),5.28–5.31(1H,m),6.11–6.21(1H,m),7.10(1H, br.s),7.36(5H,s).

IR(Nujol,cm$^{-1}$):3280,1772,1683,1554,1457.

The title compound(76B) was obtained after deprotection as described in example 43, followed by salt formation.

Yield:38%.

$^1$H NMR(D$_2$O,δ):2.72–2.88(1H,m),2.91(1H,d,J=13.3), 3.39(1H,dd,J=2.6, 16.3),3.50(2H,d,J=5.3),3.70–4.20(4H, m),4.462H,m),5.46(1H,d, J=2.6).

IR(Nujol,cm$^{-1}$):3360,3325,1766,1679,1630.

EXAMPLE 77

(3RS,5SR)-3-(L-2,6-N-Dibenzyloxycarbonylaminohexanoyl)oxymethyl-4-oxa-1-azabicyclo[3.2.0]heptan-7-one(77A) and (3RS,5SR)-3-(L-2,6-Diacetamidohexanoyl) oxymethyl-4-oxa-1-azabicyclo[3.2.0]heptan-7-one (77B)

According to the same procedure described in example 40, (2,6-Dibenzyloxycarbonylamino)hexanoyloxy derivative(77A) was obtained as thick oil.

Yield:76%.

$^1$H NMR(CDCl$_3$,δ):1.42–1.80(6H,m),2.73–2.86(2H,m), 3.18–3.30(3H,m), 3.91–4.52(5H,m),4386–5340(7H,m),7.33 (10H,s).

IR(Neat,cm$^{-1}$):3355,3070,2960,1781,1751,1721.

To a solution of (2,6-Dibenzyloxycarbonylamino) hexanoyloxy derivative(77A) obtained above (1.8 g,3.33 mmol) and Acetic anhydride (3.2 ml,3.33 mmol) in Ethyl acetate (100 ml) was added Palladium on activated carbon (10%,53.8% moist,2.0 g) and the mixture was hydrogenolysed at 50 psi for 2 hr. The catalyst was filtered off over a pad of celite and the solution was concentrated. Purification on a silica gel column using Ethyl acetate-acetone (1:2:5) as the eluent gave a thick oil(77B).

Yield:63%.

$^1$H NMR(CDCl$_3$,δ):1.19–1.87(6H,m),1.98(3H,s),2.04 (3H,s),2.76–2.89 (2H,m),3.14–3.34(3H,m),3.98(1H,dd,J= 11.6,7.0),4.10–4.25(2H,m), 4.47–4.58(2H,m),5.36(1H,br.s), 5.89(1H,br.t),6.49(1H,d,J=7.0).

IR(Neat,cm$^{-1}$):3320,3075,2693,1784,1762,1741,1656.

EXAMPLE 78

(3RS,5SR)-3-(L-5-acetamide-2-N-Benzyloxycarbonylaminohexanoyl)oxymethyl-4-oxa-1-azabicyclo[3.2.0]heptan-7-one(78)

To a Ethyl acetate(60 ml) solution of 2,5-dibenzyloxycarbonylamino hexanoyloxy derivative (77A), (1.0 g,1.85 mmol) was added Palladium on activated carbon (10%,1.0 g) and the mixture was hydrogenolysed at 50 psi for 2 h. The mixture was filtered through a pad of celite and cooled in an ice-bath. Acetic anhydride (0.44 ml,4.66 mmol) and Triethylamine (0.77 ml) were added and the mixture was stirred for 2 h and washed with water (60 ml) and brine. The Ethyl acetate solution was dried over Magnesium sulfate, concentrated and passed through a silica gel column chromatography using Ethyl acetate as the eluent to give an oil(78).

Yield:12%.

$^1$H NMR(CDCl$_3$,δ):1.29–1.89(6H,m),2.01(3H,s), 2.72–2.88(2H,m),3.14–3.31(3H,m),3.96(1H,dd,J=11.6,6.9), 4.13–4.29(2H,m),4.53–4.56(2H, m),4.97(1H,br.t),5.09(2H, s),5.32(1H,br.s),6.29(1H,d,J=7.0),7.34(5H,s).

IR(Nujol,cm$^{-1}$):3335,2950,1783,1740,1717,1659.

EXAMPLE 79

(3RS,5SR)-3-(L-2-N-Benzyloxycarbonylamino-3-phenylpropanoyloxymethyl-4-oxa-1-azabicyclo [3.2.0]heptan-7-one(79)

According to the same procedure described in example 43, N-protected title compound(79) was obtained.

Yield:63%.

$^1$H NMR(CDCl$_3$,δ):2.57–2.74(1H,m),2.82(1H,d,J=16.2), 3.11(2H,d, J=6.1),3.25(1H,dd,J=2.3,16.0),3.83–3.95(1H,m), 4.12–4.23(2H,m), 4.40–4.55(1H,m),4.59–4.75(1H,m),5.10 (2H,s),5.12–5.27(2H,m),7.20–7.38(10H,m).

IR(Neat,cm–1):3335,1784,1747,1722.

TEST EXAMPLE 1

In Vitro KB Cell Cytotoxicity Assay

In vitro KB cell cytoxocity assay was done by modification of the crystal violet assay (Grillis et al., Anal Biochem., 159, 109–113 (1986).

KB cells were cultivated in Eagles minimum essential medium supplemented with 10% calf serum and incubated at 37° C. in a humidified 5% CO$_2$ atmosphere to prepare a cell stock. Cells were counted using a neubauer hemocytometer and seeded in 96 well plates at 100 μl of 3×10$^4$ cells/ml and cultured for one day. Test compounds were diluted and 100 μl of the solution was added in triplicate wells to give final concentration of 10, 5, 1, 0.5, 0.1, 0.05 and 0.01 μg/ml. Control wells were identical except that test compound was absent. These were cultured for three days. Then the cells were fixed with addition of 20 μl of 25% glutaraldehyde for 15 minutes, washed with water and dried. Then stained with 100 μl of 0.05% crystal violet for 15 minutes, washed with water and dried. The wells are eluted with 100l of 0.05M $NaH_2PO_4$/ethanol (1:1 v/v) and read at $OD_{540}$ on a multiscan spectrophotometer. Inhibition value of cell growth was calculated based on optical density using the following equation;

$$\% \text{ inhibition} = \frac{\text{untreated} - \text{treated}}{\text{untreated}} \times 100$$

$TD_{50}$ values were calculated from linear regression ines of the log-logit plot.

The compound of formula (I) was assayed by this method against KB cell lines and their $TD_{50}$ values are reported in Table 1.

TEST EXAMPLE 2

In Vitro L1210 and P388 Cell Cytotoxicity Assay

In vitro :L1210 and P388 cell cytotoxicity assay was done by the method of microculture tetrazolium assay (Alley et al., Cancer Research, 48, 589–601 (1988).

L1210 and P388 cells were cultivated in RPMI 1640 medium supplemented with 10% fetal calf serum and 50 μl of 2-mercaptoethanol at 37° C. in humidified 5% $CO_2$ atmosphere to prepare a cell stock. Cells were counted using neubauer hemocytometer and seed in 96 well plates at 100 μl of $0.5 \times 10^4$ cells per ml. The test compounds were diluted and 100 μl of the solution was added in triplicate wells to give the final concentration of 10, 5, 1, 0.5, 0.1, 0.05 and 0.01 μg/ml. Control wells were identical except that the test compound was absent. These were cultured for three days. Results were assayed using the microculture tetrazolium assay briefly. 50 μl of MTT formazoan working solution (1:5 v/v in culture medium) was added to each well and cultures were incubated at 37° C. for 4 hrs. Culture plates were centrifuged at low speed for 5 minutes. All but 10–20 μl of culture medium supernatant was removed by slow aspiration and replaced by mechanical shaker and read at $OD_{540}$ on a multiscan spectrophotometer. Inhibition value of cell growth was calculated based on optical density using the following equation;

$$\% \text{ inhibition} = \frac{\text{untreated} - \text{treated}}{\text{untreated}} \times 100$$

$TD_{50}$ values were calculated from linear regression ines of the log-logit plot.

The compound of formula (I) was assayed by this method against L1210 and P388 cell lines and their $TD_{50}$ values are reported in Table 2.

TABLE 1

In Vitro Cell Toxicity of Compounds of General Formula I

| Example No. | X | R | KB Cell Cytotoxicity $TD_{50}$ μg/ml |
|---|---|---|---|
| 1 | NH | $COCH_3$ | 0.263 |
| 2 | NH | $COCH_3$ (3S, 5S) | 0.77 |
| 3 | NH | $COCH_3$ (3R, 5R) | 3.15 |
| 4 | NH | $CO(CH_2)_4CH_3$ | 0.312 |
| 5 | NH | $COCH(CH_3)_2$ | 0.181 |
| 6 | NH | $COC_6H_{11}$ (alicyclic) | 0.073 |
| 7 | NH | $COCF_3$ | 0.205 |
| 8 | NH | $COCH_2Cl$ | 0.084 |
| 9 | NH | $COCH_2N_3$ | 0.296 |
| 10 | NH | $COCH_2$-triazole (1, 2, 3) | 0.282 |
| 11 | NH | $COCH_2OCHO$ | 0.147 |
| 12 | NH | $COCH_2OH$ | 0.125 |
| 13 | NH | $CO(CH_2)_5Br$ | 0.491 |
| 14 | NH | $CO(CH_2)_5OCHO$ | 0.243 |
| 15 | NH | $CO(CH_2)_5N_3$ | 0.254 |
| 16 | NH | $CO(CH_2)_5$-triazole (1, 2, 3) | 0.318 |
| 17 | NH | $CO(CH_2)_5NHCOCH_3$ | 0.439 |
| 18 | NH | $CO(CH_2)_2$—COOH | 2.85 |
| 19 | NH | $CO(CH_2)_2$—CH=$CH_2$ | 0.266 |
| 20 | NH | COC≡CH | 0.333 |
| 21 | NH | $COOCH_2C_6H_5$ | 0.340 |
| 22 | NH | H.HCl | 0.344 |
| 23 | NH | $COC_6H_5$ | 0.088 |
| 24 | NH | $COC_6H_4OH$ (4) | 0.276 |
| 25 | NH | $COC_6H_4OCH_3$ (4) | 0.255 |
| 26 | NH | $COC_6H_3(OCH_3)_2$ (3, 4) | 0.249 |
| 27 | NH | $COC_6H_4F$ (4) | 0.24 |
| 28 | NH | $COC_6H_3F_2$ (2, 5) | 0.379 |
| 29 | NH | $COC_6H_2F_3$ (2, 4, 5) | 0.535 |
| 30 | NH | $COC_6H_4CN$ (4) | 0.378 |
| 31 | NH | $COCH_2$-thiophene (2) | 0.098 |
| 32 | NH | CO-pyridine (3) | 0.78 |
| 33 | NH | $CON(C_2H_5)_2$ | 0.246 |
| 34 | NH | $CONHCH_2$ clavam | 0.151 |
| 35 | NH | $SO_2CH_3$ | 0.198 |
| 36 | NH | $SO_2C_6H_4CH_3$ (4) | 0.338 |
| 37 | NH | $SO_2C_6H_4Cl$ (4) | 0.484 |
| 38 | NH | $SO_2C_6H_4OCH_3$ (4) | 0.158 |
| 39 | O | $COCH_2NH_2$.HCl | 0.613 |
| 40B | O | $COCH_2NHCOCH_2NH_2$.HCl | 0.636 |
| 41B | O | $COCH_2NH$—(L)—$COCH(CH_3)NH_2$.HCl | 0.295 |
| 42B | O | $COCH_2NH$—(L)—$COCH[CH(CH_3)_2]NH_2$.HCl | 0.388 |
| 43 | NH | $COCH_2NH_2$.HCl | 0.429 |
| 44 | NH | $COCH_2NHCOCH_3$ | 0.341 |
| 45B | NH | $COCH_2NH$—(L)—$COCH[CH(CH_3)_2]NH_2$.HCl | 1.97 |
| 46B | NH | $COCH_2NH$—(L)—$COCH(NH_2)CH_2COOH$ | 2.63 |
| 48B | O | (L)$COCH(CH_3)NH_2$.HCl | 0.878 |
| 49B | O | (L)$COCH(CH_3)NH$—(L)—$COCH[CH(CH_3(_2]NH_2$.HCl | 0.537 |
| 50B | NH | (L)$COCH(CH_3)NH_2$.HCl | 0.657 |
| 51B | O | (D)$COCH(CH_3)NH_2$.HCl | 0.867 |
| 52 | O | (D)$COCH(CH_3)NH$—(D)—COCH—($CH_3$) $NHCOCH_2$-thiophene (2) | 0.197 |
| 53B | NH | (D)$COCH(CH_3)NH_2$.HCl | 0.316 |
| 54B | O | (L)$COCH[CH(CH_3)_2]NH_2$.HCl | 1.9 |
| 55B | O | (L)$COCH[CH(CH_3)_2]NH$—$COCH_2NH_2$.HCl | 0.522 |
| 56B | O | (L)$COCH[CH(CH_3)_2]NH$—(L)—$COCH[CH(CH_3)_2]NH_2$.HCl | 0.283 |
| 57B | O | (L)$COCH[CH(CH_3)_2]NH$—(L)—$COCH(NH_2)CH_2COOH$ | 1.54 |
| 60B | O | (D)$COCH[CH(CH_3)_2]NH_2$.HCl | 0.903 |
| 61 | O | (D)$COCH[CH(CH_3)_2NHCOCH_3$ | 0.385 |
| 62B | O | (D)$COCH[CH(CH_3)_2]NH$—(D)—$COCH[CH(CH_3)_2]NH_2$ .HCl | 0.381 |
| 63B | NH | (L)$COCH(CH_2C_6H_5)NH_2$.HCl | 0.573 |
| 64B | NH | (L)$COCH(CH_2C_6H_5)NH$—(L)—$COCH(NH_2)CH_2COOH$ | 2.65 |

TABLE 1-continued

In Vitro Cell Toxicity of Compounds of General Formula I

| Example No. | X | R | KB Cell Cytotoxicity $TD_{50}$ μg/ml) |
|---|---|---|---|
| 65B | O | (L)COCH$_2$CH(NH$_2$)COOH | 0.451 |
| 66B | O | (L)COCH(NH$_2$)CH$_2$COOH | 0.204 |
| 67B | NH | (L)COCH(NH$_2$)CH$_2$COOH | 6.04 |
| 68B | O | (D)CO(CH$_2$)$_2$CH(NH$_2$)COOH | 0.189 |
| 69B | NH | (D)CO(CH$_2$)$_2$CH(NH$_2$)COOH | 2.47 |
| 70 | O | (L)COCH(CH$_2$OH)NHZ | 0.352 |
| 71 | O | (L)COCH(CH$_2$OH)NH—(D)—COCH(CH$_3$)NHZ | 0.549 |
| 72 | O | (L)COCH(CH$_2$OCH$_2$C$_6$H$_5$)NHZ | 1.67 |
| 73 | O | (L)COCH(CH$_2$OCH$_2$C$_6$H$_5$)NH—(D)—COCH(CH$_3$)NHZ | 2.22 |
| 74B | O | (L)COCH(CH$_2$OCH$_2$C$_6$H$_5$)NH—(L)—COCH[CH(CH$_3$)$_2$]NH$_2$.HCl | 0.669 |
| 75A | O | (L)COCH(CH$_2$OH)NHCOCH$_3$ | 1.98 |
| 75B | O | (L)COCH(CH$_2$OCOCH$_3$)NHCOCH$_3$ | 0.567 |
| 76B | NH | (L)COCH(CH$_2$OH)NH$_2$.HCl | 8.81 |
| 77A | O | (L)COCH(NHZ)(CH$_2$)$_4$NHZ | 1.18 |
| 78 | O | (L)COCH(NHCOCH$_3$)(CH$_2$)$_2$NHZ | 3.38 |

Z;Benzyloxycarbonyl

TABLE 2

In Vitro Cell Toxicity of Compounds of General Formula I Against Sensitive and Resistant Tumor Cell Lines

| | Cell Toxicity (μg/ml) | | | |
|---|---|---|---|---|
| Example No. | L-1210 (S) | L-1210 (R) | P388 (S) | P388 (R) |
| 1 | 0.103 | 0.104 | 0.103 | 0.074 |
| G0069A | 2.17 | 1.87 | 1.02 | 0.751 |
| Adriamycin | 0.004 | 0.36 | 0.003 | 0.575 |
| Vincristine | 0.002 | 0.20 | 2.95 × 10$^{-7}$ | 0.279 |

TEST EXAMPLE 3

In Vivo Antitumor Activity Against Sarcoma 180

The compounds of general formula (I) were tested in vivo against Sarcoma 180 xenografted tumor to mice as illustrated herein after.

Sarcoma 180, 5×10$^6$ cells were inoculated by S.C. to male ICR mice (6 week old) on day 0. Drugs were administered on days 1, 5 and 9. Mice were killed and tumor weight was measured on day 12 after transplantation. The percentage inhibition of tumor growth was calculated from the mean tumor weight of the treated group compared with that of the control group. Number of mice used in each group was between 6 to 7. The percentage inhibition of tumor Sarcoma 180 group by compound of formula (I) are summarized in Table 3.

TABLE 3

Effect of Compounds of Formula (I) Against Sarcoma 180 (s.c. - i.p.) in Male ICR

| Example No. | Dose (mg/kg/day) | Mortality in 12 days | % Inhibition |
|---|---|---|---|
| 1 | 12.5 | 0/6 | 71.4 |
| | 6.25 | 0/6 | 49.3 |
| | 3.1 | 0/6 | 33.9 |
| 2 | 20 | 1/7 | 77.5 |
| | 10 | 0/6 | 44.7 |
| 4 | 100 | 0/6 | 49.4 |
| 6 | 80 | 0/6 | 43.3 |
| | 40 | 0/6 | 35.7 |
| | 20 | 0/6 | 32.1 |
| 7 | 100 | 2/6 | 39.8 |
| 8 | 35 | 1/6 | 64.0 |
| | 17.5 | 0/6 | 51.3 |
| | 8.8 | 0/6 | 39.0 |
| 22 | 80 | 0/6 | 40.3 |
| | 40 | 0/6 | 26.7 |
| 23 | 100 | 0/6 | 27.8 |
| 31 | 40 | 1/6 | 35.5 |
| 33 | 90 | 0/6 | 74.5 |
| | 45 | 0/6 | 66.2 |
| | 22.5 | 0/6 | 46.6 |
| 34 | 25 | 5/6 | 92.5 |
| | 12.5 | 0/6 | 76.3 |
| | 6.25 | 0/6 | 59.8 |
| 35 | 100 | 1/6 | 64.6 |
| 38 | 100 | 1/6 | 72.0 |
| | 50 | 0/6 | 55.4 |
| | 25 | 0/6 | 26.5 |
| 39 | 50 | 0/6 | 76.7 |
| | 25 | 0/6 | 56.7 |
| | 12.5 | 0/6 | 41.9 |
| 40B | 50 | 0/6 | 72.0 |
| | 25 | 0/6 | 54.0 |
| | 12.5 | 0/6 | 48.3 |
| 41B | 25 | 0/6 | 62.8 |
| | 12.5 | 0/6 | 43.9 |
| 42B | 50 | 0/6 | 85.8 |
| | 25 | 0/6 | 69.0 |
| | 12.5 | 0/6 | 49.9 |
| 43 | 50 | 0/6 | 72.1 |
| | 25 | 0/6 | 58.9 |
| | 12.5 | 0/6 | 57.0 |
| | 6.3 | 0/6 | 48.7 |
| 44 | 25 | 4/6 | 85.3 |
| | 12.5 | 0/6 | 45.9 |
| 45B | 50 | 0/6 | 81.7 |
| | 25 | 0/6 | 39.3 |
| 46B | 50 | 1/6 | 76.9 |
| | 25 | 0/6 | 55.7 |
| | 12.5 | 0/6 | 44.7 |
| 48B | 50 | 2/6 | 77.3 |
| | 25 | 0/6 | 66.8 |
| | 12.5 | 0/6 | 44.9 |
| 49B | 50 | 0/6 | 71.0 |
| | 25 | 0/6 | 55.7 |
| 51B | 100 | 5/6 | 93.8 |
| | 50 | 0/6 | 82.4 |
| | 25 | 0/6 | 50.6 |
| | 12.5 | 0/6 | 40.9 |
| 52 | 100 | 2/6 | 70.7 |
| | 50 | 0/6 | 63.9 |
| | 25 | 0/6 | 45.2 |
| 53B | 25 | 1/6 | 73.8 |
| | 12.5 | 0/6 | 61.9 |
| | 6.3 | 0/6 | 47.3 |
| 54B | 100 | 0/6 | 84.3 |
| | 50 | 0/6 | 53.8 |
| | 25 | 0/6 | 28.5 |
| 55B | 50 | 0/6 | 74.4 |
| | 25 | 0/6 | 47.6 |
| 56B | 50 | 0/6 | 73.2 |
| | 25 | 0/6 | 69.2 |
| | 12.5 | 0/6 | 48.9 |
| 57B | 50 | 1/6 | 83.1 |
| | 25 | 0/6 | 58.1 |
| | 12.5 | 0/6 | 40.9 |
| 60B | 100 | 0/6 | 77.7 |

TABLE 3-continued

Effect of Compounds of Formula (I) Against Sarcoma 180 (s.c. - i.p.) in Male ICR

| Example No. | Dose (mg/kg/day) | Mortality in 12 days | % Inhibition |
|---|---|---|---|
|  | 50 | 0/6 | 49.8 |
| 62B | 100 | 0/6 | 42.1 |
| 63B | 100 | 0/6 | 57.6 |
|  | 50 | 0/6 | 50.3 |
| 66B | 25 | 0/6 | 62.9 |
|  | 12.5 | 0/6 | 53.2 |
|  | 6.3 | 0/6 | 33.7 |
| 65B | 100 | 0/6 | 55.0 |
| 67B | 100 | 0/6 | 65.9 |
|  | 50 | 0/6 | 41.1 |
| 68B | 50 | 3/6 | 80.3 |
|  | 25 | 0/6 | 69.7 |
|  | 12.5 | 0/6 | 49.1 |
| 69B | 100 | 0/6 | 37.8 |
| 74B | 100 | 1/6 | 84.1 |
|  | 50 | 0/6 | 49.9 |
| 75A | 25 | 0/6 | 61.9 |
|  | 12.5 | 0/6 | 42.8 |
| 75B | 50 | 4/6 | 77.8 |
|  | 25 | 0/6 | 65.1 |
|  | 12.5 | 0/6 | 37.8 |
| 77A | 100 | 2/6 | 67.3 |
|  | 50 | 0/6 | 39.1 |

We claim:

1. A compound of formula I or a pharmaceutically acceptable salt thereof,

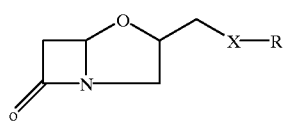

(I)

wherein when X is NH,
R is (a) hydrogen, (b) —$COR_1$ wherein $R_1$ is (i) a $C_1$–$C_6$ alkyl group which may be substituted by 1–3 substituents selected from halogen, hydroxy, formyloxy, azido, carboxyl, heteroaryl or acetamide, (ii) a $C_2$–$C_4$ alkenyl group, (iii) a $C_2$–$C_4$ alkynyl group, (iv) a $C_3$–$C_6$ cycloalkyl group, (v) a phenyl group which may be substituted by 1–3 substituents selected from hydroxy, halogen, $C_1$–$C_6$ alkoxy group or cyano, (vi) a heteroaryl group having 5–6 ring atoms of which 1–3 atoms are heteroatoms selected from the group consisting of nitrogen and sulfur, (vii) a $NR_2R_3$ group wherein $R_2$ and $R_3$ are the same or different and each is a hydrogen, $C_1$–$C_6$ alkyl group or (7-oxo-1-aza-4-oxabicyclo[3.2.0]hept-3-yl)methyl group or (viii) benzyloxy group;
(c) —$SO_2R_4$ wherein $R_4$ is a $C_1$–$C_6$ alkyl group or a phenyl group which may be substituted by 1–3 substituents selected from $C_1$–$C_6$ alkyl group, halogen or $C_1$–$C_6$ alkoxy group; or
(d) the group remaining after the removal of the hydroxy group from a carboxy group of 1–2 naturally occurring α-amino acids or their optical isomers, wherein the group may be substituted with protective group, and wherein when X is O,
R is the group remaining after the removal of the hydroxy group from a carboxy group of 1–2 naturally occurring α-amino acids or their optical isomers, wherein the group may be substituted with protective group.

2. The compound as set forth in claim 1 wherein X is NH and R is —$COR_1$ wherein $R_1$ is $C_1$–$C_6$ alkyl group which may be substituted by 1–3 substituents selected from halogen, hydroxy, formyloxy, azido, carboxy, heteroaryl or acetamido.

3. The compound as set forth in claim 1 wherein X is NH and R is —$COR_1$ wherein $R_1$ is a $NR_2R_3$ wherein $R_2$ and $R_3$ are the same or different and each is a hydrogen, $C_1$–$C_6$ alkyl group or (7-oxo-1-aza-4-oxabicyclo[3.2.0]hept-3-yl)methyl group.

4. The compound as set forth in claim 1, wherein X is NH or O and R is the group remaining after the removal of the hydroxy group from a carboxy group of 1–2 naturally occurring α-amino acids or their optical isomers, wherein the group may be substituted with protective group.

5. The compound as set forth in claim 1 wherein X is NH, having (3R,5R) or (3S,5S) configuration at two asymmetric carbons on 4-oxa-1-azabicyclo[3.2.0]heptan-7-one ring system or the mixture of them.

6. The compound as set forth in claim 1 wherein X is O, having (3R,5S) or (3S,5R) configuration at two asymmetric carbons on 4-oxa-1-azabiyclo[3.2.0]heptan-7-one ring system or the mixture of them.

7. A pharmaceutical composition comprising of a compound as set forth in claim 1 and pharmaceutically acceptable carrier.

8. A process for preparing a compound as set forth in claim 1
wherein when X is O,
said process comprising reacting a compound having general formula II with substituted carboxylic acid in the presence of a base in a solvent,

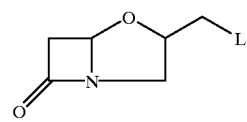

(II)

and wherein when X is NH,
said process comprising converting the compound having general formula II to amino by reaction with metal azide followed by reduction in presence of metal catalyst and reacting the resulting amino compound with acid halide, acid anhydride or activated ester in the presence of a base in a solvent,
wherein L is an appropriate leaving group.

9. A method of treating cancer selected from stomach, lung, breast, liver and uterus cancer and leukemia, in a patient in need thereof, the method comprising administering to the patient a cancer treating-effective amount of a compound as set forth in claim 1.

* * * * *